US010786323B2

(12) United States Patent
Ang et al.

(10) Patent No.: US 10,786,323 B2
(45) Date of Patent: Sep. 29, 2020

(54) HANDHELD SURGICAL INSTRUMENT, SURGICAL TOOL SYSTEM, METHODS OF FORMING AND OPERATING THE SAME

(71) Applicant: Nanyang Technological University, Singapore (SG)

(72) Inventors: Wei Tech Ang, Singapore (SG); Zenan Wang, Singapore (SG)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 159 days.

(21) Appl. No.: 16/078,263

(22) PCT Filed: Mar. 23, 2017

(86) PCT No.: PCT/SG2017/050147
§ 371 (c)(1),
(2) Date: Aug. 21, 2018

(87) PCT Pub. No.: WO2017/164818
PCT Pub. Date: Sep. 28, 2017

(65) Prior Publication Data
US 2019/0076203 A1 Mar. 14, 2019

(30) Foreign Application Priority Data

Mar. 23, 2016 (SG) .............................. 10201602287P

(51) Int. Cl.
*A61B 34/00* (2016.01)
*A61B 17/062* (2006.01)
(Continued)

(52) U.S. Cl.
CPC ............ *A61B 34/72* (2016.02); *A61B 17/062* (2013.01); *A61B 34/75* (2016.02); *A61B 90/20* (2016.02);
(Continued)

(58) Field of Classification Search
USPC .............................. 700/245–264; 606/1, 130
See application file for complete search history.

(56) References Cited

U.S. PATENT DOCUMENTS

2011/0106102 A1* 5/2011 Balicki ............... A61F 9/00727
606/130
2013/0016185 A1* 1/2013 Stolka .................. A61B 8/5238
348/46
(Continued)

FOREIGN PATENT DOCUMENTS

WO WO 2012/012540 A2 1/2012
WO WO 2014/165593 A1 10/2014

OTHER PUBLICATIONS

Ang, W. T. et al., *Active Tremor Compensation in Microsurgery*, Proceedings of the 26th Annual International Conference of the IEE EMBS (Sep. 2004) 2738-2741.
(Continued)

*Primary Examiner* — Jonathan L Sample
(74) *Attorney, Agent, or Firm* — Alston & Bird LLP

(57) ABSTRACT

Various embodiments provide a handheld surgical instrument including a laser source configured to emit a laser beam for generating a laser marker on a surface, an inertial measurement unit configured to detect a motion of the handheld surgical instrument and generate a first signal including information on the motion of the handheld surgical instrument detected by the inertial measurement unit, and a movable platform for holding a controlled tool tip. The handheld surgical instrument additionally includes an actuator mechanically coupled to the movable platform, and a processing circuit configured to control the actuator to move the movable platform based on the first signal generated by the inertial measurement unit and a second signal generated by a vision unit based on a movement of the laser marker, so that the movement of the movable platform at least partially compensates a tremulous motion of the handheld surgical instrument.

20 Claims, 30 Drawing Sheets

(51) Int. Cl.
*A61B 90/98* (2016.01)
*A61B 90/20* (2016.01)
*A61B 17/00* (2006.01)
*A61B 90/30* (2016.01)
*A61B 34/20* (2016.01)
*A61B 90/00* (2016.01)

(52) U.S. Cl.
CPC .... *A61B 90/98* (2016.02); *A61B 2017/00694* (2013.01); *A61B 2034/2048* (2016.02); *A61B 2034/2055* (2016.02); *A61B 2090/309* (2016.02); *A61B 2090/3937* (2016.02)

(56) References Cited

U.S. PATENT DOCUMENTS

| | | | | |
|---|---|---|---|---|
| 2013/0123759 | A1* | 5/2013 | Kang | A61B 34/70 606/1 |
| 2014/0005484 | A1* | 1/2014 | Charles | A61B 17/3211 600/201 |
| 2014/0303643 | A1* | 10/2014 | Ha | A61B 34/37 606/130 |
| 2015/0018622 | A1* | 1/2015 | Tesar | A61B 50/13 600/202 |
| 2015/0182285 | A1* | 7/2015 | Yen | A61B 34/76 606/80 |
| 2015/0272694 | A1* | 10/2015 | Charles | A61B 90/37 600/202 |
| 2015/0305761 | A1* | 10/2015 | Kang | A61B 17/28 606/205 |
| 2016/0030240 | A1* | 2/2016 | Gonenc | G01L 25/00 604/95.01 |
| 2016/0113724 | A1* | 4/2016 | Stolka | A61B 8/4444 600/424 |
| 2016/0119529 | A1* | 4/2016 | Stolka | A61B 8/4444 348/211.1 |
| 2016/0135900 | A1* | 5/2016 | Falardeau | A61F 2/4609 600/424 |
| 2016/0220315 | A1* | 8/2016 | Falardeau | A61B 34/20 |
| 2016/0220391 | A1* | 8/2016 | Duval | A61B 5/1075 |

OTHER PUBLICATIONS

Ang, W. T. et al., *An Active Hand-Held Instrument for Enhanced Microsurgical Accuracy*, MICCAI, LNCS 1935, Springer-Verlag Berlin Heidelberg (2000) 878-886.

Aye, Y. N. et al., *An Active Handheld Instrument Aided with Virtual Fixtures for Real-Time Micromanipulation Using fusion of Vision and Inertial Sensing*, 3$^{rd}$ IFToMM International Symposium on Robotics and Mechatronics (2013) 10 pages.

Aye, Y. N. et al., *An Enhanced Intelligent Handheld Instrument With Visual Servo Control For 2-DOF Hand Motion Error Compensation*, International Journal of Advanced Robotic Systems, vol. 10 (2013) 8 pages.

Aye, Y. N. et al., *Fusion of Inertial Measurements and Vision Feedback for Microsurgery*, Intelligent Autonomous Systems 12. Advances in Intelligent Systems and Computing, Springer, Berlin, Heidelberg 2013, vol. 194 (Jun. 26, 2012) 27-35.

Becker, B. C. et al., *Semiautomated Intraocular Laser Surgery Using Handheld Instruments*, Lasers in Surgery and Medicine 42 (2010) 264-273.

Latt, W. T. et al., *A Compact Hand-Held Active Physiological Tremor Compensation Instrument*, IEEE/ASME International Conference on Advanced Intelligent Mechatronics (Jul. 2009) 711-716.

MacLachlan, R. A. et al., *Micron: An Actively Stabilized Handheld Tool for Microsurgery*, IEE Transactions on Robotics, vol. 28, No. 1 (Feb. 2012) 17 pages.

Song, C. et al., *Active Tremor Cancellation by a "Smart" Handheld Vitreoretinal Microsurgical Tool Using Swept Source Optical Coherence Tomography*, Optics Express, vol. 20, No. 21 (Oct. 2012) 23414-23421.

Tan, U.-X. et al., *A Low-Cost Flexure-Based Handheld Mechanism for Micromanipulation*, IEEE/ASME Transactions on Mechatronics, vol. 16., No. 4 (Aug. 2011) 773-778.

Tatinati, S. et al., *Multidimensional Modeling of Physiological Tremor for Active Compensation in Handheld Surgical Robotics*, IEEE Transactions on Industrial Electronics, vol. 64, No. 2 (Feb. 2017) 1645-1655.

Taylor, R. et al., *A Steady-Hand Robotic System for Microsurgical Augmentation*, The International Journal of Robotics Research (Dec. 1999) 1201-1210.

International Search Report and Written Opinion for Application No. PCT/SG2017/050147 dated Jun. 9, 2017, 12 pages.

Extended European Search Report for Application No. EP 17 77 0727 dated Oct. 15, 2019, 12 pages.

Tighe, S. M., *Instrumentation for the Operating Room* . . . [online][retrieved Oct. 2, 2019]. Retrieved via the Internet: https://books.google.de/books?id=N2KGBwAAQBAJ&dq=surgical+tool+tip+laser+drill+scissor+forcep&source=gbs_navlinks_s (Oct. 2, 2019) p. 60, 3 pages.

* cited by examiner

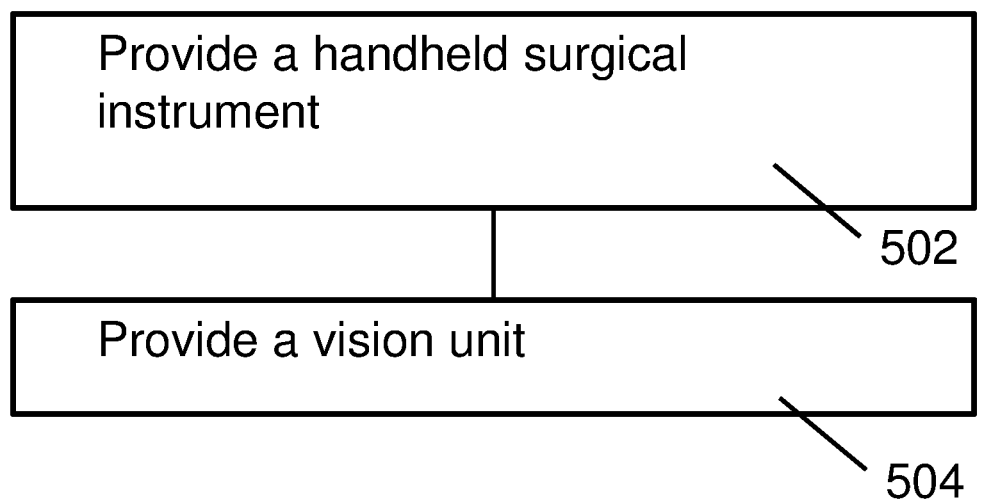

| Tip Displacement | Max Peak-Peak (μm) | Attenuation (%) | Root Mean Square (μm) | Attenuation (%) |
|---|---|---|---|---|
| Uncompensated | 253 | 61.3 | 60 | 73.3 |
| Compensated | 98 | | 16 | |

| Design | Micron II | ITrem2 |
|---|---|---|
| Standard deviation of angular acceleration with respect to X axis (rad/s$^2$) | 0.102 | 0.086 |
| Standard deviation of angular acceleration with respect to Y axis (rad/s$^2$) | 0.704 | 0.103 |
| Standard deviation of angular acceleration with respect to Z axis (rad/s$^2$) | 0.704 | 0.951 |
| Standard deviation of linear acceleration along X axis (mm/s$^2$) | 57.10 | 13.69 |
| Standard deviation of linear acceleration along Y axis (mm/s$^2$) | 17.21 | 12.92 |
| Standard deviation of linear acceleration along Z axis (mm/s$^2$) | 7.07 | 9.90 |
| Resultant standard deviation of tool tip linear acceleration | 59.82 | 21.05 |

| Competitive Analysis | Proposed Instrument/ System | Intuitive Surgical, Inc. (Da Vinci System) |
|---|---|---|
| Positioning accuracy | Max error < 100 μm; RMS error < 20 μm | Approximate fiducial localization error (FLE): 1 mm |
| Cost | Initial: US$5K<br>Operating (per surgery): US$500 | Initial: > US$1M<br>Operating (per surgery): >US$10k |
| Dexterity | Inherits the full dexterity of human hands | Limited by the 6 DOF arms and inertia of the arms. |
| Size | Small handheld instrument ⌀22x170mm, 80g | Large telerobotic arms and console |

|  | Proposed Instrument/ System Device | CMU Device |
|---|---|---|
| Size & Weight | ⌀22x170mm, 80g | ⌀28.5x126mm, 70g |
| Error reduction performance | max ε: 253→98μm; 61.2% reduction<br>rmse: 60→16μm; 73.3% reduction | max ε: 301→103μm; 65.7% reduction<br>rmse: 93→40μm; 57.0% reduction |

HANDHELD SURGICAL INSTRUMENT, SURGICAL TOOL SYSTEM, METHODS OF FORMING AND OPERATING THE SAME

CROSS-REFERENCE TO RELATED APPLICATION

This application is a national phase entry of PCT/SG2017/050147, filed on Mar. 23, 2017, which claims the benefit of priority of Singapore application No. 10201602287P filed on Mar. 23, 2016, the contents of it being hereby incorporated by reference in its entirety for all purposes.

TECHNICAL FIELD

Various aspects of this disclosure relate to handheld surgical instruments and/or surgical tool systems. Various aspects of this disclosure relate to methods of forming handheld surgical instruments and/or surgical tool systems. Various aspects of this disclosure relate to methods of operating handheld surgical instruments and/or surgical tool systems.

BACKGROUND

The hand motion of a person has involuntary movements such as physiological tremor, myoclonic jerk, drift, etc., which limits the ability of the person to perform accurate and precise manual micromanipulation tasks, especially when the magnitude of the intended motion and erroneous movements are of similar order. Tasks such as microsurgery or cell manipulation in the bio-tech industry may be significantly hampered, while tasks such as handling guns, military handheld tracking equipment or consumer video cameras may be slightly or moderately hampered.

In microsurgery, the involuntary movements may complicate many delicate surgical procedures, and may also make certain types of intervention impossible (e.g. intraocular cannulation for the treatment of retinal vein occlusions by injection of anticoagulants without tearing the retinal vein apart). The high level of manual precision and accuracy demanded by microsurgery restrict the number of people which can be qualified as surgeons. The fact that human hand stability deteriorates with age further exacerbates the situation and limits the career lifespan of these surgeons. In addition, factors such as fatigue, alcohol and caffeine consumption, and other factors may affect the manual stability of hand movements of surgeons.

In general, there are currently 3 robotics based approaches to enhance human manual positioning precision and accuracy in microsurgery.

The first approach involves the use of telerobotic technology, in which a robotic arm is used to replace the unstable human hand. Currently, there are no specialized robotic devices for microsurgery in the market and the closest commercially available system would be the Da Vinci Robotic Surgery System by Intuitive Surgical, Inc. (USA). This approach filters erroneous motion between master and slave manipulators via motion scaling. Though effective, this approach is costly and obtrusive for the surgeon, who may be accustomed to treating the patient with his own hands. A robotic arm with the requisite workspace also introduces significant safety and liability issues. The telerobotic solution may cause catastrophic damages when a malfunction happens. In addition, the Da Vinci surgical system is designed for general surgery and is not a specialized surgical instrument for microsurgery.

The second approach involves a surgeon and a robot, such as the Steady-Hand Eye Robot from John Hopkins University, directly manipulating the same tool. The robot has high stiffness. When the surgeon applies a manual input force to the tool, the tool is moved along directions deemed desirable by the robot. While this system cannot scale input motion, it has advantages in terms of cost and likelihood of user acceptance. Moreover, it provides the surgeon a "third hand" to hold a tool in position while the surgeon performs other tasks with his own two hands. However, the "steady hand" solution can also cause catastrophic damages in the event of any malfunction. This robotic system has been last reported to be in the proof-of-concept phase in June 2013.

The last approach relates to assistive handheld instruments, such as "Micron" by Professor Cameron Riviere from Carnegie Mellon University. The "Micron" device depends on a custom-built position sensitive detector (PSD) based optical tracking system which has limited sensing volume (<8 $cm^3$: 2×2×2 cm). The line of sight between the infrared emitters mounted on the device and the PSD must not be interrupted. Such a setup would be impractical for real clinical deployment.

SUMMARY

Various embodiments may provide a handheld surgical instrument. The handheld surgical instrument may include a laser source configured to emit a laser beam for generating a laser marker on a surface, e.g. a human or an animal body. The handheld surgical instrument may also include an inertial measurement unit configured to detect a motion of the handheld surgical instrument and generate a first signal including information on the motion of the handheld surgical instrument detected by the inertial measurement unit. The handheld surgical instrument may further include a movable platform for holding a controlled tool tip. The handheld surgical instrument may additionally include an actuator mechanically coupled to the movable platform. The handheld surgical instrument may also include a processing circuit configured to control the actuator to move the movable platform based on the first signal generated by the inertial measurement unit and a second signal generated by a vision unit based on a movement of the laser marker, so that the movement of the movable platform holding the controlled tool tip at least partially compensates a tremulous motion of the handheld surgical instrument.

Various embodiments may provide a surgical tool system. The surgical tool system may include a handheld surgical instrument. The handheld surgical instrument may include a laser source configured to emit a laser beam for generating a laser marker on a surface. The handheld surgical instrument may also include an inertial measurement unit configured to detect a motion of the handheld surgical instrument and generate a first signal including information on the motion of the handheld surgical instrument detected by the inertial measurement unit. The handheld surgical instrument may additionally include a movable platform for holding a controlled tool tip. The handheld surgical instrument may further include an actuator mechanically coupled to the movable platform. The handheld surgical instrument may also include a processing circuit configured to control the actuator to move the movable platform based on the first signal generated by the inertial measurement unit and a second signal. The surgical tool system may further include a vision unit configured to detect a movement of the laser marker, and further configured to generate the second signal, the second signal include information on the movement of the laser marker detected by the vision unit. The processing circuit may be configured to control the actuator so that the movement of the movable platform holding the controlled tool tip at least partially compensates a tremulous motion of the handheld surgical instrument.

Various embodiments may provide a method of operating a handheld surgical instrument. The method may include using a laser source to emit a laser beam to generate a laser marker on a surface. The method may also include detecting, using inertial measurement unit, a motion of the handheld surgical instrument. The method may include generating, using the inertial measurement unit, a first signal including information on the motion of the handheld surgical instrument detected. The method may additionally include controlling, using a processing circuit, an actuator to move a movable platform, the movable platform holding a controlled tool tip, based on the first signal generated by the inertial measurement unit and a second signal generated by a vision unit based on a movement of the laser marker, so that the movement of the movable platform holding the controlled tool tip at least partially compensates a tremulous motion of the handheld surgical instrument.

Various embodiments may provide a method of operating a surgical tool system. The method may include operating a handheld surgical instrument so that a laser beam is emitted from a laser source to generate a laser marker on a surface. The method may also include operating the handheld surgical instrument to detect a motion of the handheld surgical instrument using an inertial measurement unit, and generate a first signal comprising information on the motion of the handheld surgical instrument detected by the inertial measurement unit. The method may further include operating a vision unit to detect a movement of the laser marker, and to generate a second signal, the second signal comprising information on the movement of the laser marker detected by the vision unit. The handheld surgical instrument may include a processing circuit configured to control an actuator to move a movable platform, the movable platform mechanically coupled to the actuator and holding a controlled tool tip, based on the first signal generated by the inertial measurement unit and the second signal generated by the vision unit so that the movement of the movable platform holding the controlled tool tip at least partially compensates a tremulous motion of the handheld surgical instrument.

Various embodiments may provide a method of forming a handheld surgical instrument. The method may include providing a laser source configured to emit a laser beam for generating a laser marker on a surface. The method may also include providing an inertial measurement unit configured to detect a motion of the handheld surgical instrument and generate a first signal including information on the motion of the handheld surgical instrument detected by the inertial measurement unit. The method may further include providing a movable platform for holding a controlled tool tip. The method may additionally include mechanically coupling an actuator to the movable platform. The method may further include electrically connecting a processing circuit to the actuator, the processing circuit configured to control the actuator to move the movable platform based on the first signal generated by the inertial measurement unit and a second signal generated by a vision unit based on a movement of the laser marker, so that the movement of the movable platform holding the controlled tool tip at least partially compensates a tremulous motion of the handheld surgical instrument.

Various embodiments may provide a method of forming a surgical tool system. The method may include providing a handheld surgical instrument. The handheld surgical instrument may include a laser source configured to emit a laser beam for generating a laser marker on a surface, an inertial measurement unit configured to detect a motion of the handheld surgical instrument and generate a first signal comprising information on the motion of the handheld surgical instrument detected by the inertial measurement unit, a movable platform for holding a controlled tool tip, an actuator mechanically coupled to the movable platform, and a processing circuit configured to control the actuator to move the movable platform based on the first signal generated by the inertial measurement unit and a second signal. The method may also include providing a vision unit configured to detect a movement of the laser marker, and further configured to generate the second signal, the second signal comprising information on the movement of the laser marker detected by the vision unit. The processing circuit may be configured to control the actuator so that the movement of the movable platform holding the controlled tool tip at least partially compensates a tremulous motion of the handheld surgical instrument.

BRIEF DESCRIPTION OF THE DRAWINGS

The invention will be better understood with reference to the detailed description when considered in conjunction with the non-limiting examples and the accompanying drawings, in which:

FIG. 5 shows a schematic of a method for forming a surgical tool system according to various embodiments.

FIG. 9C is a table showing the numerical uncompensated results and the compensated results according to various embodiments.

FIG. 10C shows a table comparing the performance of ITrem2 according to various embodiments with MicronII.

FIG. 14A is a table comparing various parameters of the instrument/system according to various embodiments and the Da Vinci System (Tele-operated Surgical Robotics System).

FIG. 14B is a table comparing various parameters of the instrument/system according to various embodiments and the Micron handheld instrument.

DETAILED DESCRIPTION

Figure 1A:
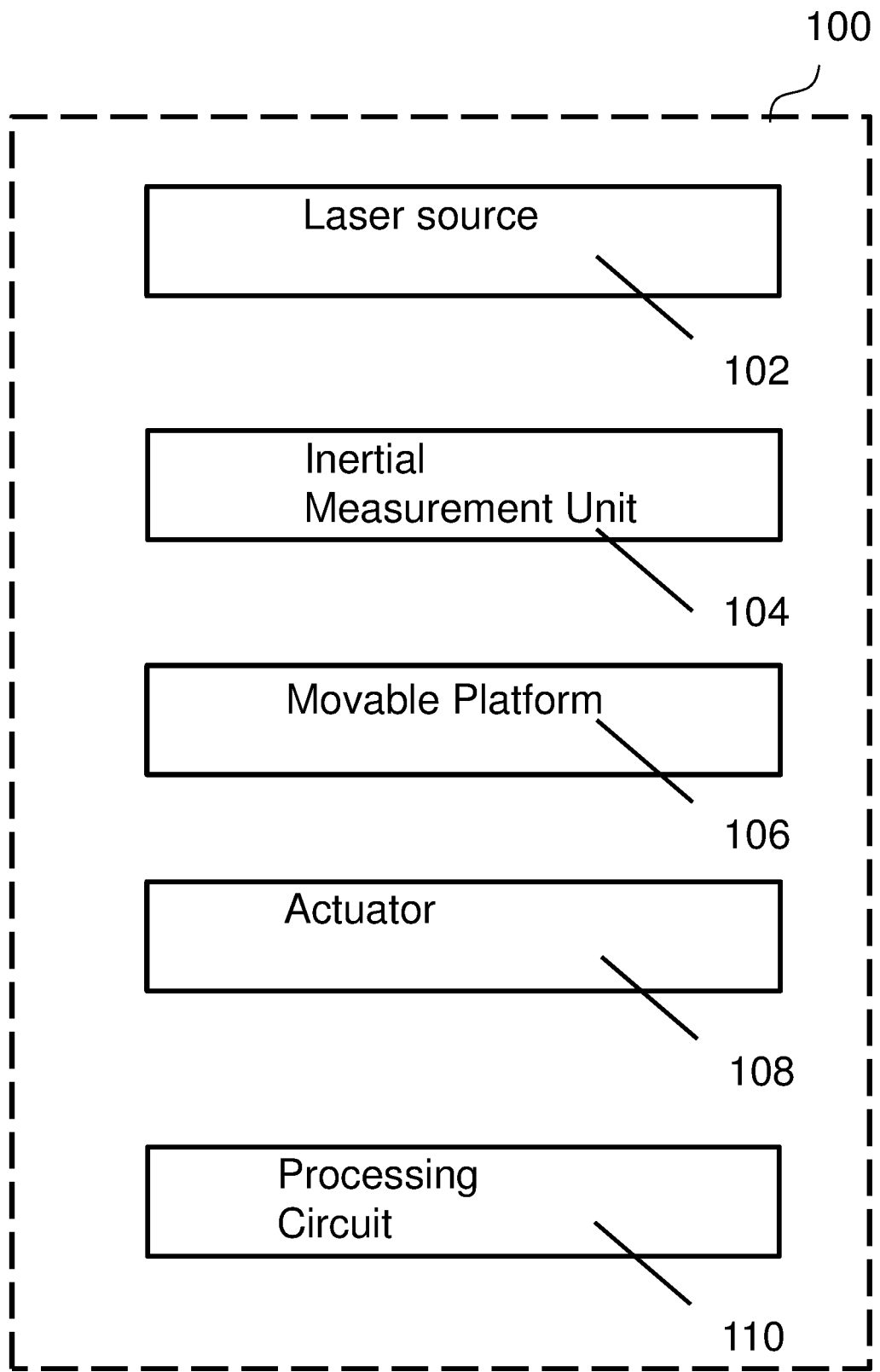
FIG. 1A shows a general illustration of a handheld surgical instrument according to various embodiments.

The following detailed description refers to the accompanying drawings that show, by way of illustration, specific details and embodiments in which the invention may be practiced. These embodiments are described in sufficient detail to enable those skilled in the art to practice the invention. Other embodiments may be utilized and structural, and logical changes may be made without departing from the scope of the invention. The various embodiments are not necessarily mutually exclusive, as some embodiments can be combined with one or more other embodiments to form new embodiments.

Embodiments described in the context of one of the methods or instruments/systems are analogously valid for the other methods or instruments/systems. Similarly, embodiments described in the context of a method are analogously valid for a instrument/system, and vice versa.

Features that are described in the context of an embodiment may correspondingly be applicable to the same or similar features in the other embodiments. Features that are described in the context of an embodiment may correspondingly be applicable to the other embodiments, even if not explicitly described in these other embodiments. Furthermore, additions and/or combinations and/or alternatives as described for a feature in the context of an embodiment may correspondingly be applicable to the same or similar feature in the other embodiments.

The word "over" used with regards to a deposited material formed "over" a side or surface, may be used herein to mean that the deposited material may be formed "directly on", e.g. in direct contact with, the implied side or surface. The word "over" used with regards to a deposited material formed "over" a side or surface, may also be used herein to mean that the deposited material may be formed "indirectly on" the implied side or surface with one or more additional layers being arranged between the implied side or surface and the deposited material. In other words, a first layer "over" a second layer may refer to the first layer directly on the second layer, or that the first layer and the second layer are separated by one or more intervening layers.

The instrument/device as described herein may be operable in various orientations, and thus it should be understood that the terms "top", "bottom", etc., when used in the following description are used for convenience and to aid understanding of relative positions or directions, and not intended to limit the orientation of the instrument/system.

In the context of various embodiments, the articles "a", "an" and "the" as used with regard to a feature or element include a reference to one or more of the features or elements.

In the context of various embodiments, the term "about" or "approximately" as applied to a numeric value encompasses the exact value and a reasonable variance.

As used herein, the term "and/or" includes any and all combinations of one or more of the associated listed items.

Various embodiments may seek to provide a solution that addresses, mitigates or overcomes the abovementioned issues.

The hand motion of a person, such as a surgeon, may include tremulous motion, such as physiological tremors, which are high frequency movements (e.g. about 5 Hz to 12 Hz), and non-tremulous motion such as drift motion and myoclonic jerk motion, which are low frequency movements (e.g. less than 8 Hz, e.g. about 0 to about 2 Hz or about 0 to about 1 Hz).

Various embodiments may provide a handheld surgical instrument. The handheld instrument may be configured to at least partially compensate for the tremulous motion of a hand of the surgeon holding the handheld surgical device. The handheld instrument may compensate for a motion by controlling the controlled tool tip to move in an opposing direction as the motion. By compensating for the tremulous motion of the hand, various embodiments may allow the surgeon to more accurately and precisely perform surgical operations.

A surgeon as described herein may be a person performing a surgical operation on a subject, such as on a human or an animal.

FIG. 1A shows a general illustration of a handheld surgical instrument 100 according to various embodiments. The handheld surgical instrument 100 may include a laser source 102, such as a laser diode, configured to emit a laser beam for generating a laser marker on a surface, e.g. a human or an animal body. The handheld surgical instrument 100 may also include an inertial measurement unit 104 configured to detect a motion of the handheld surgical instrument 100 and generate a first signal including information on the motion of the handheld surgical instrument 100 detected by the inertial measurement unit 104. The handheld surgical instrument 100 may further include a movable platform 106 for holding a controlled tool tip. The handheld surgical instrument 100 may additionally include an actuator 108, such as a piezoelectric actuator, mechanically coupled to the movable platform 106. The handheld surgical instrument 100 may also include a processing circuit 110, such as an embedded microcontroller, configured to control the actuator 108 to move the movable platform 106 based on the first signal generated by the inertial measurement unit 104 and a second signal generated by a vision unit based on a movement of the laser marker, so that the movement of the movable platform 106 holding the controlled tool tip at least partially compensates a tremulous motion of the handheld surgical instrument 100.

In other words, the handheld surgical instrument 100 may include two mechanisms to compensate for a tremulous motion of the handheld surgical instrument 100. The instrument 100 may include an inertial measurement unit 104 configured to detect motion of the handheld surgical instrument 100, and a laser source 102 which generates a laser marker, which may be tracked by a vision unit separate from the instrument 100 to detect the motion of the handheld surgical instrument 100. The instrument 100 may include an actuator 108 configured to move a movable platform 106, which holds a controlled tool tip. The movement of the platform 106 may be based on inputs provided by the inertial measurement unit 104 and the vision unit to help compensate for a tremulous motion of the handheld surgical instrument 100 to a processing circuit coupled to the actuator 108.

The instrument 100 may be an untethered handheld device with on-board power source or alternatively, tethered to an external power source. The instrument 100 may be referred to as an assistive handheld microsurgical instrument. The instrument 100 may be capable of sensing its own motion with on-board inertial sensors comprised in the inertial measurement unit 104.

In various embodiments, the laser beam may include visible light. In various embodiments, the laser beam may include infrared light which may be detected by the vision unit but may not be seen directly by the surgeon, thereby reducing glare on the surgeon.

In various embodiments, the instrument 100 may be configured to generate a single laser marker.

In various other embodiments, the instrument 100 may be configured to generate two laser markers. The handheld surgical instrument 100 may further include a beam splitter configured to separate the laser beam to form the laser marker and a further laser marker on the surface. The second signal may be generated by the vision unit based on the movement of the laser marker and a movement of the further laser marker. The use of two laser markers may help track a pan angle of the instrument 100. The inertial measurement unit 104 may be configured to determine the tilt angle of the instrument. The pan angle of the instrument may be determined based on the tilt angle, roll angle and/or orientations of the two laser markers.

The laser beam may produce a laser marker of any suitable shape on the surface. For instance, the laser marker may be of any shape selected from a group consisting of a circular shape, a rectangular shape, a T-shape, and a cross shape. A non-circular laser marker may also help track the pan angle of the instrument 100.

The inertial measurement unit 104 may include one or more accelerometers or inertia sensors for detecting the motion of the handheld surgical instrument 100, such as a movement of the controlled tool tip. The one or more accelerometers may be configured to measure an acceleration of the instrument 100 or the controlled tool tip. For instance, each accelerometer may include a proof mass which deflects from a neutral position when the accelerometer undergoes acceleration. The acceleration may be determined by detecting a capacitance between an electrode on the proof mass and a reference electrode. The accelerometer may be a microelectromechanical system (MEMs) device.

In various embodiments, the first signal (generated by the inertial measurement unit 104) may include information on the motion of the handheld surgical instrument 100 within a range of frequencies, e.g. about 0 Hz-about 400 Hz, including a frequency of intended motion of the surgical instrument, e.g. about 0 Hz-about 1 Hz. In various embodiments, the second signal (generated by the vision unit) may include information on the movement of the laser marker above a predetermined threshold, e.g. about 1 Hz or about 2 Hz, the predetermined threshold set above the frequency of intended motion of the surgical instrument, e.g. about 0 Hz-about 1 Hz.

The processing circuit 110 may be configured to control the actuator 108 to move the movable platform 106 based on the first signal and the second signal so that the intented motion of the surgical instrument (at e.g. about 0-about 1 Hz) is uncompensated by the movement of the movable platform.

The inertial measurement unit 104 may have an acquisition frequency of up to 400 Hz. The vision unit may have an image acquisition speed of up to 100 frames per second (fps), and may be able to detect movement of the laser marker up to about 100 Hz. The speed of the vision unit may be dependent on the shutter speed and/or the computing speed to process the image of the laser marker(s). Motion/movement at least up to about 100 Hz may thus be detected by both the inertial measurement unit 104 and the vision unit. A high pass filter may be used to separate different frequency components of the movement of the laser marker detected by the vision unit at a predetermined threshold or cutoff value, e.g. at about 1 Hz. Accordingly, the second signal transmitted from the vision unit to the processing circuit 110 may include information on the movement of the laser marker at frequencies above the predetermined threshold or cutoff value of about 1 Hz, i.e. in the range of about 1 Hz-about 100 Hz. On the other hand, the inertial measurement unit 104 may be able to detect movement from 0 Hz up to at least up to 400 Hz. By integrating the information on the movement of the laser marker detected by the vision unit with information on the motion of the handheld surgical instrument 100 detected by the inertial measurement unit 104, intended motion of instrument by the surgeon (e.g. at about 0 Hz-about 1 Hz) may be determined or identified by the processing circuit 110, and subsequently not compensated by the actuator 108. The processing circuit 110 may be configured to determine or identify information in the frequency range of about 5 Hz-about 12 Hz from information comprised in the first signal and the second signal to compensate for the tremulous motion in the range of about 5 Hz to about 12 Hz. While the inertial measurement unit 104 and the vision unit may be able to detect motion/movement at least up to about 100 Hz, only tremulous motion in the range of about 5 Hz to about 12 Hz may be compensated. Drift motion of the instrument 100 at for instance about 0 Hz to about 1 Hz may not be compensated. In various embodiments, the ranges recited herein may be inclusive of both end values.

The inertial measurement unit 104 alone may not be able to accurately determine the low frequency motion (e.g. about 0 Hz-about 1 Hz) due to the intented motion of the instrument and the drift motion, as the accelerometer noise may be greater than the magnitude of acceleration of low frequency movements such as hand motion drift, thus distorting readings in the low frequency range (e.g. about 0 Hz to about 1 Hz). By using one or more laser markers to track the motion and subsequently using a high pass filter to filter away movements in the low frequency range (e.g. about 0 Hz to about 1 Hz), various embodiments may improve accuracy in compensation of movements above the threshold e.g. about 5 Hz to about 12 Hz. The inclusion of the inertial measurement unit 104 may allow real time sensing as the inertial measurement unit 104 has a higher sensing/sampling rate compared to the vision unit. The use of a laser beam instead of a physical marker may allow the instrument 100 to be non-obtrusive.

In various embodiments, the handheld surgical instrument 100 may include the controlled tool tip. The controlled tool tip may be a disposable and/or replaceable tip. The controlled tool tip may be a micro-forceps, a micro-needle holder, a micro-scissor, or a micro-surgical needle/blade. The controlled tool tip may be reversibly attached to the movable platform 106. In other words, the controlled tool tip may be easily attached and detached from the movable platform 106. The movable platform 106 may include a mechanism, such as an adaptor, to attach or hold the controlled tool tip. The controlled tool tip may be snap onto the adaptor.

In various embodiments, the instrument 100 may control the controlled tool tip to fully compensate a tremulous motion of the handheld surgical instrument 100 by controlling the controlled tool tip to move in an equal and opposite direction to the tremulous motion.

The handheld surgical instrument 100 may include a power source or a holder for a power source. The power source may be configured to provide power to the laser source 102, the inertial measurement unit 104, the actuator 108, and/or the processing circuit 110.

Figure 1B:
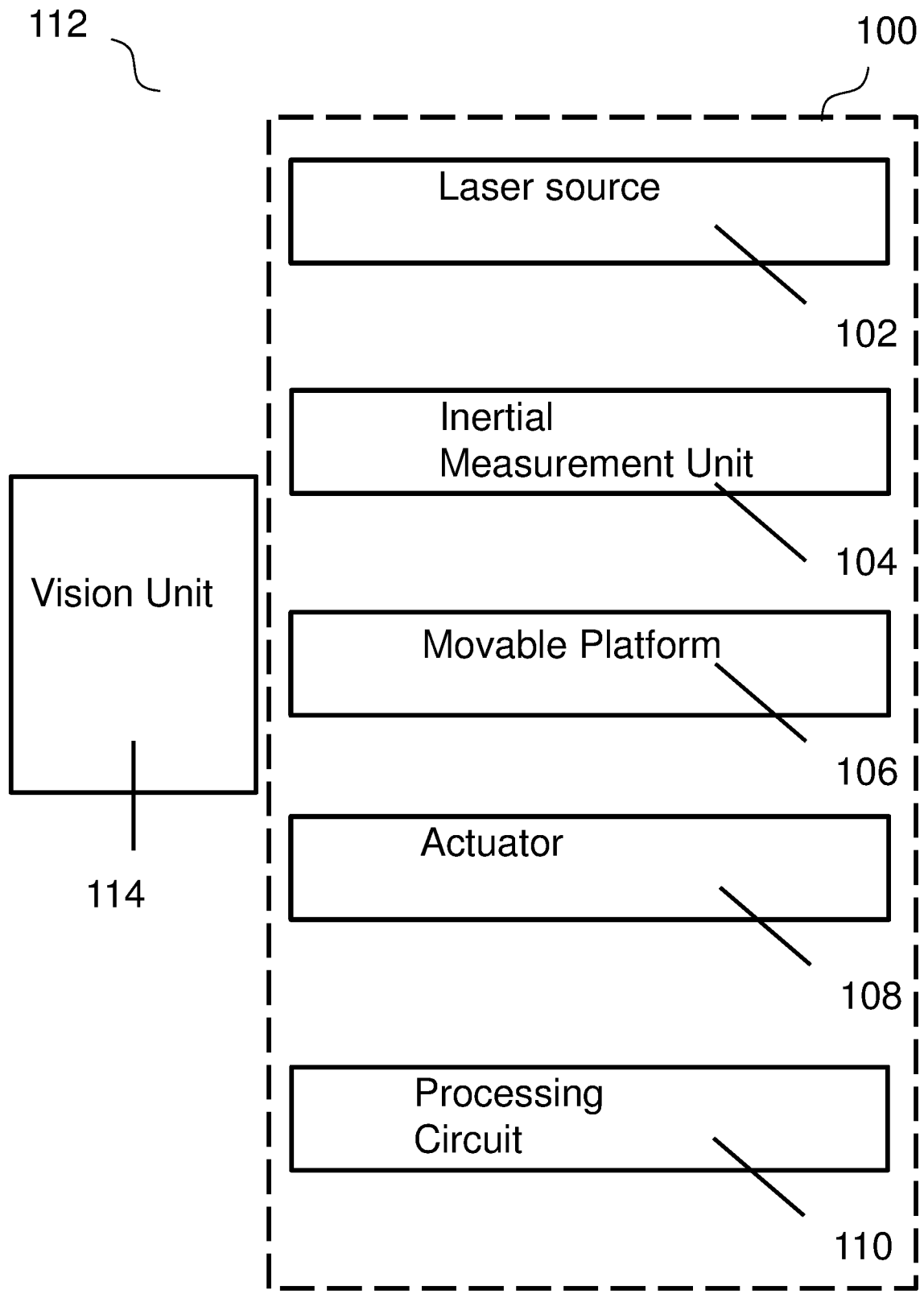
FIG. 1B shows a general illustration of a surgical tool system according to various embodiments.

FIG. 1B shows a general illustration of a surgical tool system 100 according to various embodiments. The surgical tool system 112 may include a handheld surgical instrument 100 as shown in FIG. 1A. The handheld surgical instrument 100 may include a laser source 102 configured to emit a laser beam for generating a laser marker on a surface. The handheld surgical instrument 100 may also include an inertial measurement unit 104 configured to detect a motion of the handheld surgical instrument 100 and generate a first signal including information on the motion of the handheld surgical instrument 100 detected by the inertial measurement unit 104. The handheld surgical instrument 100 may additionally include a movable platform 106 for holding a controlled tool tip. The handheld surgical instrument 100 may further include an actuator 108 mechanically coupled to the movable platform 106. The handheld surgical instrument 100 may also include a processing circuit 110 configured to control the actuator 108 to move the movable platform 106 based on the first signal generated by the inertial measurement unit and a second signal.

The surgical tool system 112 may further include a vision unit 114 configured to detect a movement of the laser marker, and further configured to generate the second signal, the second signal include information on the movement of the laser marker detected by the vision unit 114. The processing circuit 110 may be configured to control the actuator 108 so that the movement of the movable platform 106 holding the controlled tool tip at least partially compensates a tremulous motion of the handheld surgical instrument 100.

The vision unit 114 may include a camera configured to detect the movement of the laser marker by converting an optical signal generated by the laser marker into an electrical signal.

The vision unit 114 may further include a surgical microscope configured to magnify laser marker.

The vision unit 114 may additionally include a computer configured to receive the electrical signal from the camera. The computer may be further configured to determine a centroid of the laser marker. Information on the movement of the laser marker may be information on a movement of the centroid of the laser marker.

The computer may be configured to generate and transmit the second signal to the processing circuit 110 of the handheld surgical instrument 100. The computer may be configured to transmit the second signal to the processing circuit 110, e.g. an embedded microcontroller, via wireless communications (e.g. Wi-Fi, Zig-bee, Bluetooth, infrared, etc.) or wired communications.

The computer may be further configured to filter out the movement of the laser marker at or below a predetermined threshold (e.g. by using a high pass filter), so that the second signal includes information on a movement of the laser marker above the predetermined threshold.

The predetermined threshold may be set above a frequency of intended motion of the surgical instrument. The predetermined threshold may be about 1 Hz or about 2 Hz.

The first signal (generated by the inertial measurement unit 104) may include information on the motion of the handheld surgical instrument 100 within a range of frequencies (e.g. about 0 Hz up to at least about 400 Hz) including the frequency of intended motion of the surgical instrument 100 (about 0 Hz to about 1 Hz).

The processing circuit 110 may be configured to control the actuator 108 to move the movable platform 106 based on the first signal and the second signal so that the intented motion of the surgical instrument 100 is uncompensated by the movement of the movable platform.

The processing circuit 110 may be configured to generate an output signal based on the first signal and the second signal, the output signal excluding frequencies at or below the predetermined threshold. The processing circuit 110 may be configured to control the actuator 108 to move the movable platform 106 based on the output signal. The information on the motion of the handheld surgical instrument detected by the inertial measurement unit may be or may include information of the acceleration of the controlled tool tip. The information on the movement of the laser marker detected by the vision unit may be or may include information on the position of the controlled tool tip.

A position of the one or more laser markers as detected by the vision unit may have a corresponding time stamp.

In various embodiments, the computer of the vision unit 114 or the processing circuit 110 may be configured to determine an acceleration of the controlled tool tip at a time corresponding to the time stamp, by interpolating acceleration values at neighbouring time stamps from information detected by the vision unit 114. The computer of the vision unit 114 or the processing circuit 110 may also be configured to determine a velocity or/and a position of the controlled tool tip at the time based on the acceleration of the controlled tool tip at the time.

The computer of the vision unit 114 or the processing circuit 110 may be further configured to predict a position of the controlled tool tip at a latter specified time based on the position, velocity and acceleration of the controlled tool tip at the time. By predicting the position of the controlled tool tip at the latter specified time, the actuator 108 may be controlled to move the movable platform so that the controlled tool tip is moved before the latter specified time, thereby offsetting a delay associated with the actuator 108.

Figure 2:
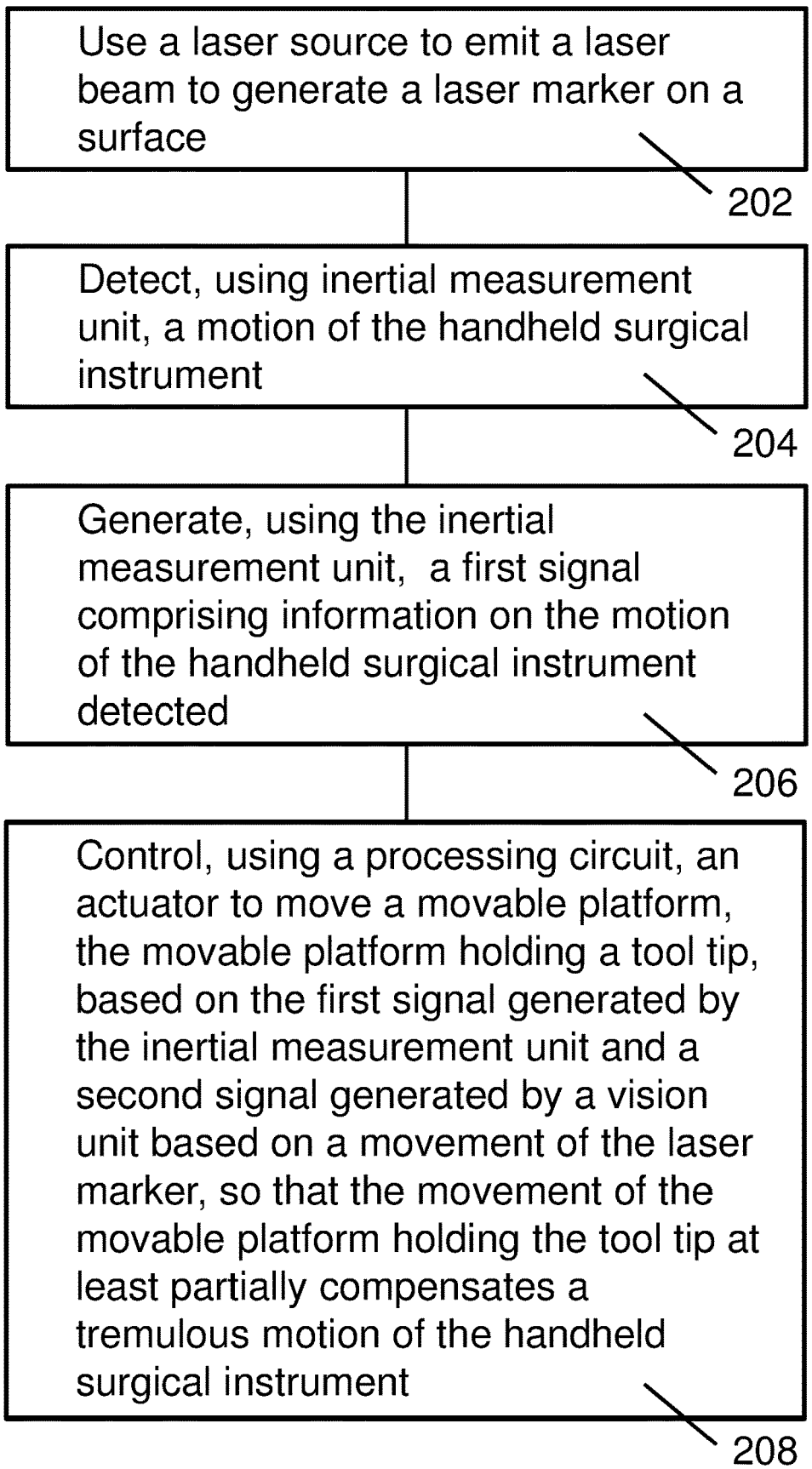
FIG. 2 is a schematic showing a method of operating a handheld surgical instrument according to various embodiments.

FIG. 2 is a schematic 200 showing a method of operating a handheld surgical instrument according to various embodiments. The method may include, in 202, using a laser source to emit a laser beam to generate a laser marker on a surface. The method may also include, in 204, detecting, using inertial measurement unit, a motion of the handheld surgical instrument. The method may include, in 206, generating, using the inertial measurement unit, a first signal including information on the motion of the handheld surgical instrument detected. The method may additionally include, in 208, controlling, using a processing circuit, an actuator to move a movable platform, the movable platform holding a controlled tool tip, based on the first signal generated by the inertial measurement unit and a second signal generated by a vision unit based on a movement of the laser marker, so that the movement of the movable platform holding the controlled tool tip at least partially compensates a tremulous motion of the handheld surgical instrument.

In other words, the method may include tracking a laser marker, detecting using an inertial measurement unit, and using the data from the laser marker and data from the inertial measurement to control a movable platform holding a tool top so as to help compensate a tremulous motion of the handheld surgical instrument.

In various embodiments, the laser beam may include visible light or infrared light.

The method may further include using a beam splitter to separate the laser beam to form the laser marker and a further laser marker on the surface. The second signal may be generated by the vision unit based on the movement of the laser marker and a movement of the further laser marker.

The laser beam may produce a laser marker of any suitable shape on the surface. For instance, the laser marker may be of any shape selected from a group consisting of a circular shape, a rectangular shape, a T-shape, and a cross shape.

The inertial measurement unit may include one or more accelerometers for detecting the motion of the handheld surgical instrument.

The first signal (generated by the inertial measurement unit) may include information on the motion of the handheld surgical instrument within a range of frequencies including a frequency of intended motion of the surgical instrument.

The second signal (generated by the vision unit) may include information on the movement of the laser marker above a predetermined threshold (e.g. about 1 Hz or about 2 Hz), the predetermined threshold set above the frequency of intended motion of the surgical instrument (e.g. about 0 Hz-about 1 Hz).

The processing circuit may be configured to control the actuator to move the movable platform based on the first signal and the second signal so that the intented motion of the surgical instrument is uncompensated by the movement of the movable platform.

Figure 3:
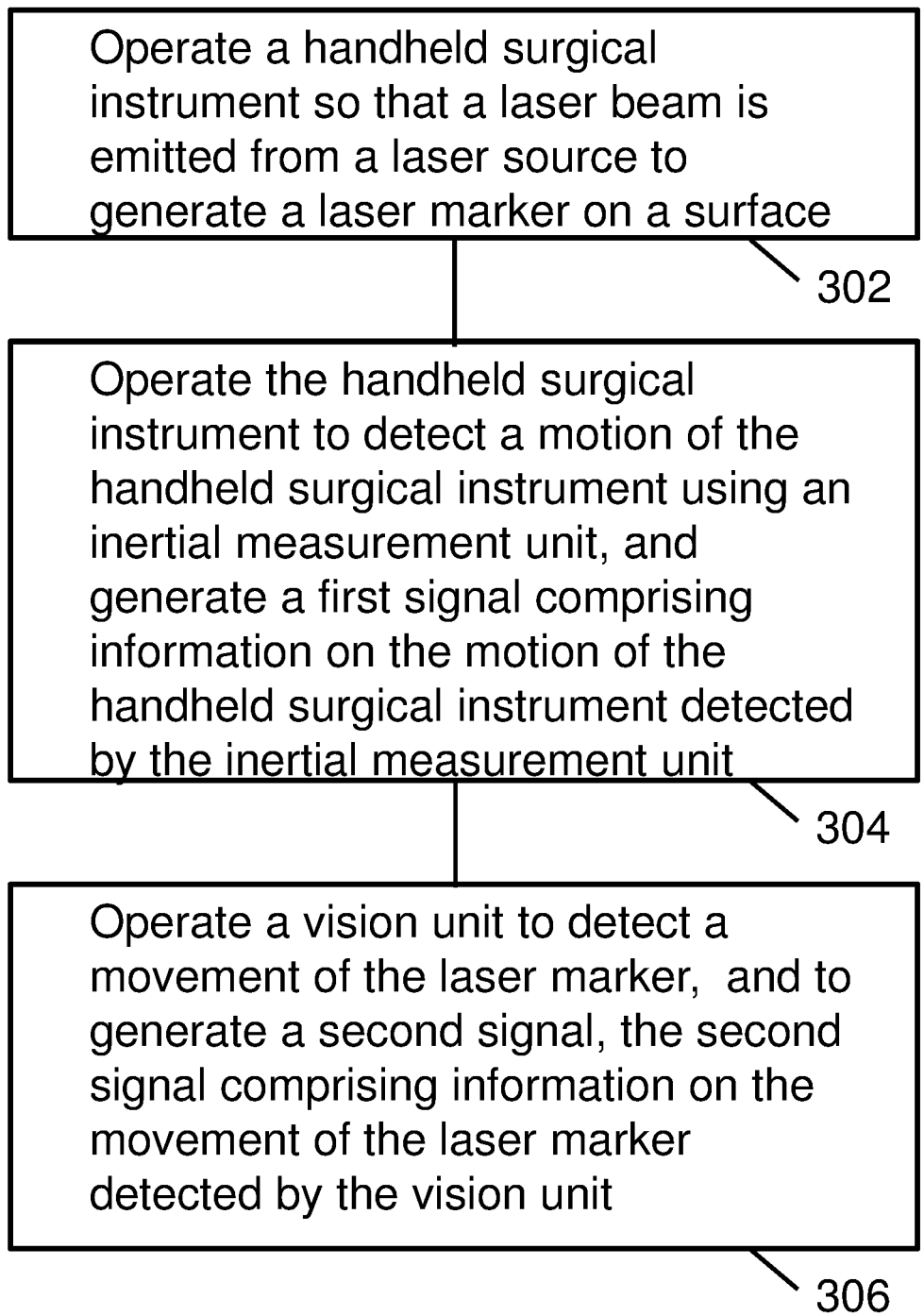
FIG. 3 is a schematic showing a method of operating a surgical tool system according to various embodiments.

FIG. 3 is a schematic 300 showing a method of operating a surgical tool system according to various embodiments. The method may include, in 302, operating a handheld surgical instrument so that a laser beam is emitted from a laser source to generate a laser marker on a surface. The method may also include, in 304, operating the handheld surgical instrument to detect a motion of the handheld surgical instrument using an inertial measurement unit, and generate a first signal comprising information on the motion of the handheld surgical instrument detected by the inertial measurement unit. The method may further include, in 306, operating a vision unit to detect a movement of the laser marker, and to generate a second signal, the second signal comprising information on the movement of the laser marker detected by the vision unit. The handheld surgical instrument may include a processing circuit configured to control an actuator to move a movable platform, the movable platform mechanically coupled to the actuator and holding a controlled tool tip, based on the first signal generated by the inertial measurement unit and the second signal generated by the vision unit so that the movement of the movable platform holding the controlled tool tip at least partially compensates a tremulous motion of the handheld surgical instrument.

The laser beam may include visible light or infrared light.

The handheld surgical instrument further may include a beam splitter configured to separate the laser beam to form the laser marker and a further laser marker on the surface. The vision unit may be operated to detect the movement of the laser marker and a movement of the further laser marker.

The laser beam may produce a laser marker of any suitable shape on the surface. For instance, the laser marker may be of any shape selected from a group consisting of a circular shape, a rectangular shape, a T-shape, and a cross shape.

In various embodiments, the inertial measurement unit may include one or more accelerometers for detecting the motion of the handheld surgical instrument.

The movement of the laser marker may be detected by using a camera comprised in the vision unit, the camera configured to convert an optical signal generated by the laser marker into an electrical signal.

The laser marker may be magnified by a surgical microscope comprised in the vision unit.

The vision unit may include a computer configured to receive the electrical signal from the camera. The computer may be further configured to determine a centroid of the laser marker. Information on the movement of the laser marker may be information on a movement of the centroid of the laser marker.

The computer may be configured to generate and transmit the second signal to the processing circuit of the handheld surgical instrument. The computer may be further configured to filter out (e.g. using a high pass filter) the movement of the laser marker at or below a predetermined threshold (e.g. about 1 Hz or about 2 Hz)), so that the second signal includes information on a movement of the laser marker above the predetermined threshold. The predetermined threshold may be set above a frequency of intended motion of the surgical instrument (e.g. about 0-1 Hz).

On the other hand, the first signal may include information on the motion of the handheld surgical instrument within a range of frequencies including the frequency of intended motion of the surgical instrument.

The processing circuit may be configured to control the actuator to move the movable platform based on the first signal and the second signal so that the intented motion of the surgical instrument is uncompensated by the movement of the movable platform.

The processing circuit may be configured to generate an output signal based on the first signal and the second signal, the output signal excluding frequencies at or below the predetermined threshold. The processing circuit may be configured to control the actuator to move the movable platform based on the output signal.

Figure 4:
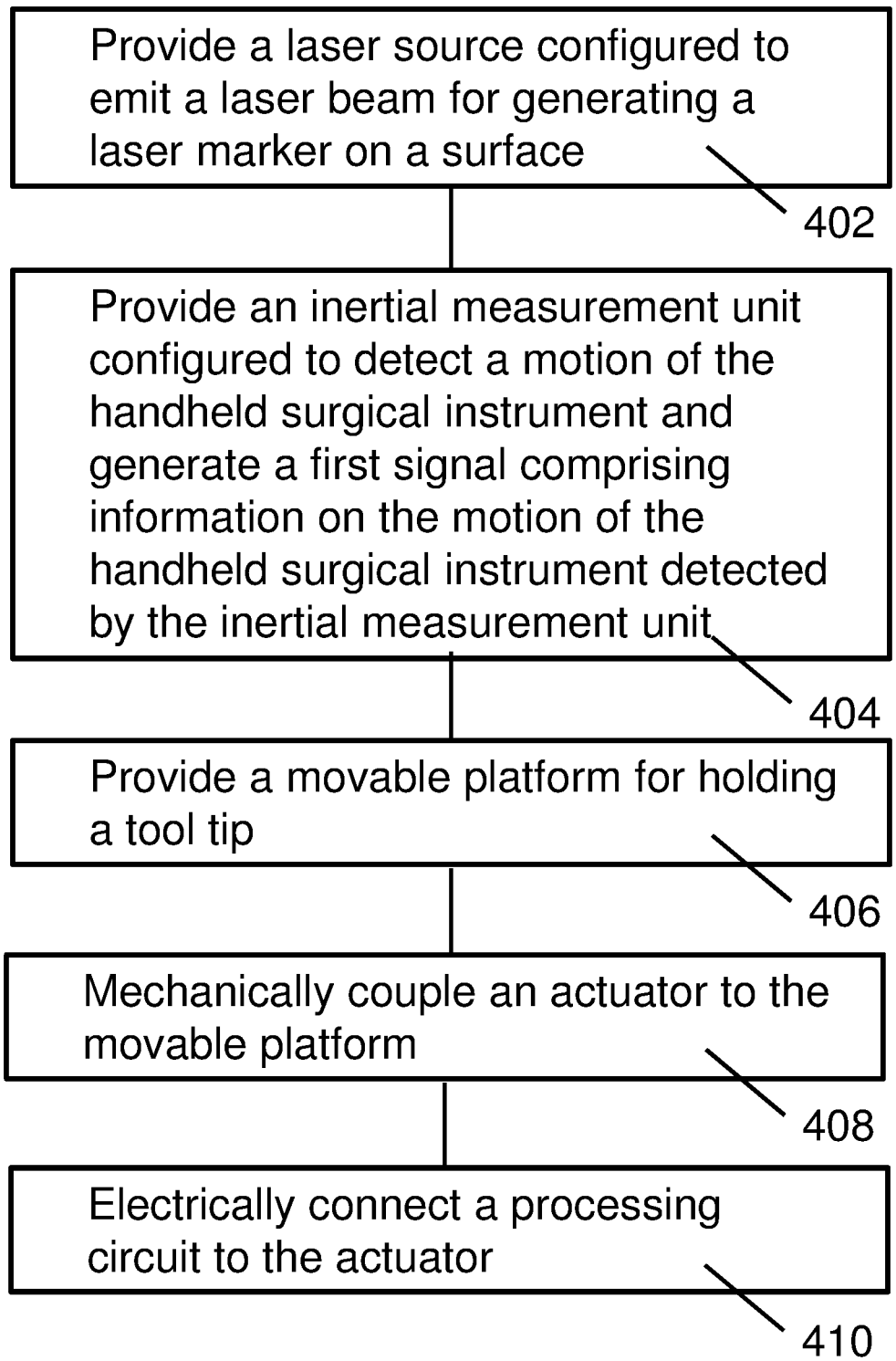
FIG. 4 shows a schematic of a method for forming a handheld surgical instrument according to various embodiments.

FIG. 4 shows a schematic of a method for forming a handheld surgical instrument according to various embodiments. The method may include, in 402, providing a laser source configured to emit a laser beam for generating a laser marker on a surface. The method may also include, in 404, providing an inertial measurement unit configured to detect a motion of the handheld surgical instrument and generate a first signal comprising information on the motion of the handheld surgical instrument detected by the inertial measurement unit. The method may further include, in 406, providing a movable platform for holding a controlled tool tip. The method may additionally include, in 408, mechanically coupling an actuator to the movable platform. The method may further include, in 410, electrically connecting a processing circuit to the actuator, the processing circuit configured to control the actuator to move the movable platform based on the first signal generated by the inertial measurement unit and a second signal generated by a vision unit based on a movement of the laser marker, so that the movement of the movable platform holding the controlled tool tip at least partially compensates a tremulous motion of the handheld surgical instrument.

In other words, the method may provide a method of fabricating or assembling a handheld surgical instrument as described herein.

FIG. 5 shows a schematic of a method for forming a surgical tool system according to various embodiments. The method may include, in 502, providing a handheld surgical instrument. The handheld surgical instrument may include a laser source configured to emit a laser beam for generating a laser marker on a surface, an inertial measurement unit configured to detect a motion of the handheld surgical instrument and generate a first signal comprising information on the motion of the handheld surgical instrument detected by the inertial measurement unit, a movable platform for holding a controlled tool tip, an actuator mechanically coupled to the movable platform, and a processing circuit configured to control the actuator to move the movable platform based on the first signal generated by the inertial measurement unit and a second signal. The method may also include, in 504, providing a vision unit configured to detect a movement of the laser marker, and further configured to generate the second signal, the second signal comprising information on the movement of the laser marker detected by the vision unit. The processing circuit may be configured to control the actuator so that the movement of the movable platform holding the controlled tool tip at least partially compensates a tremulous motion of the handheld surgical instrument.

In other words, the method may include a method of forming or setting up a surgical tool system as described herein. The method may include providing a handheld surgical instrument and a vision unit as described herein.

Figure 6A:
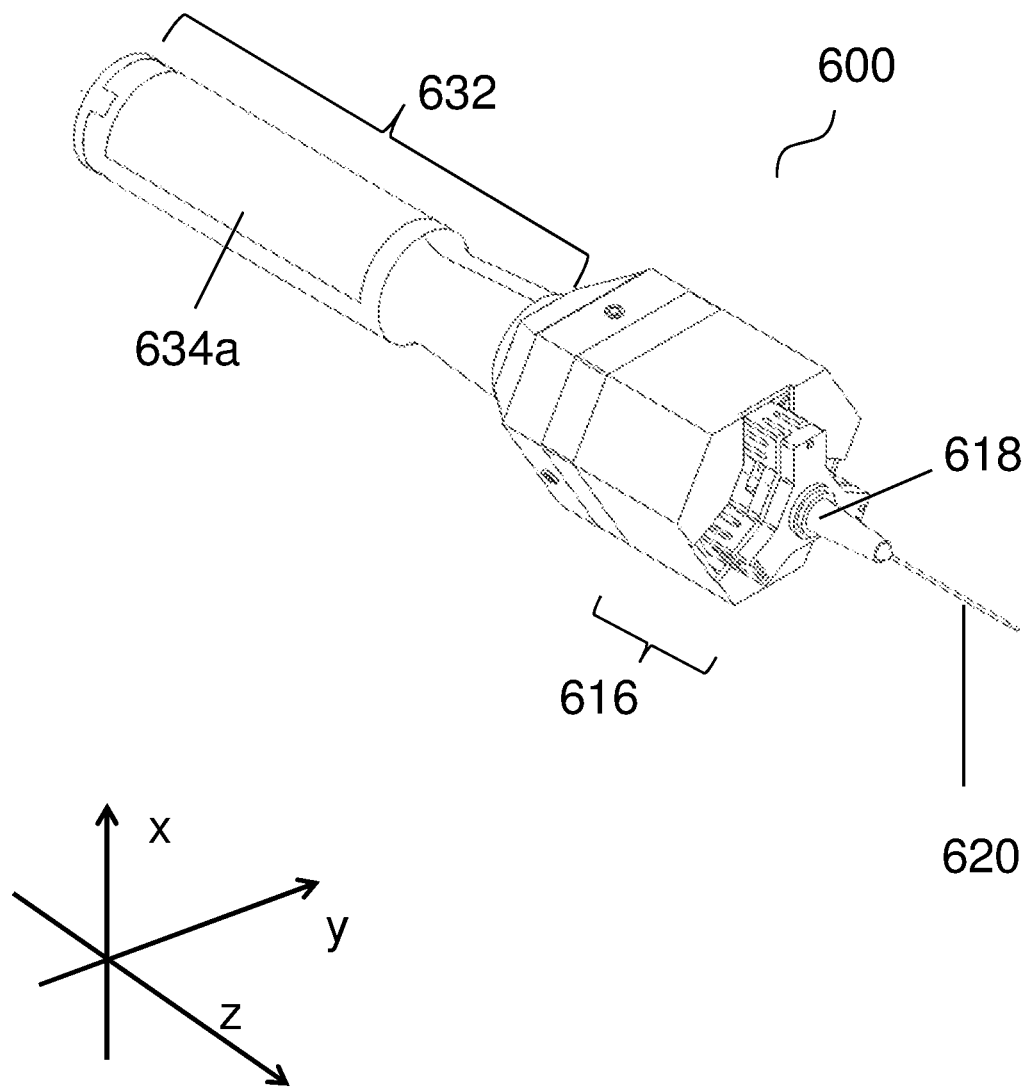
FIG. 6A shows an external view of a handheld surgical instrument according to various embodiments.
Figure 6B:
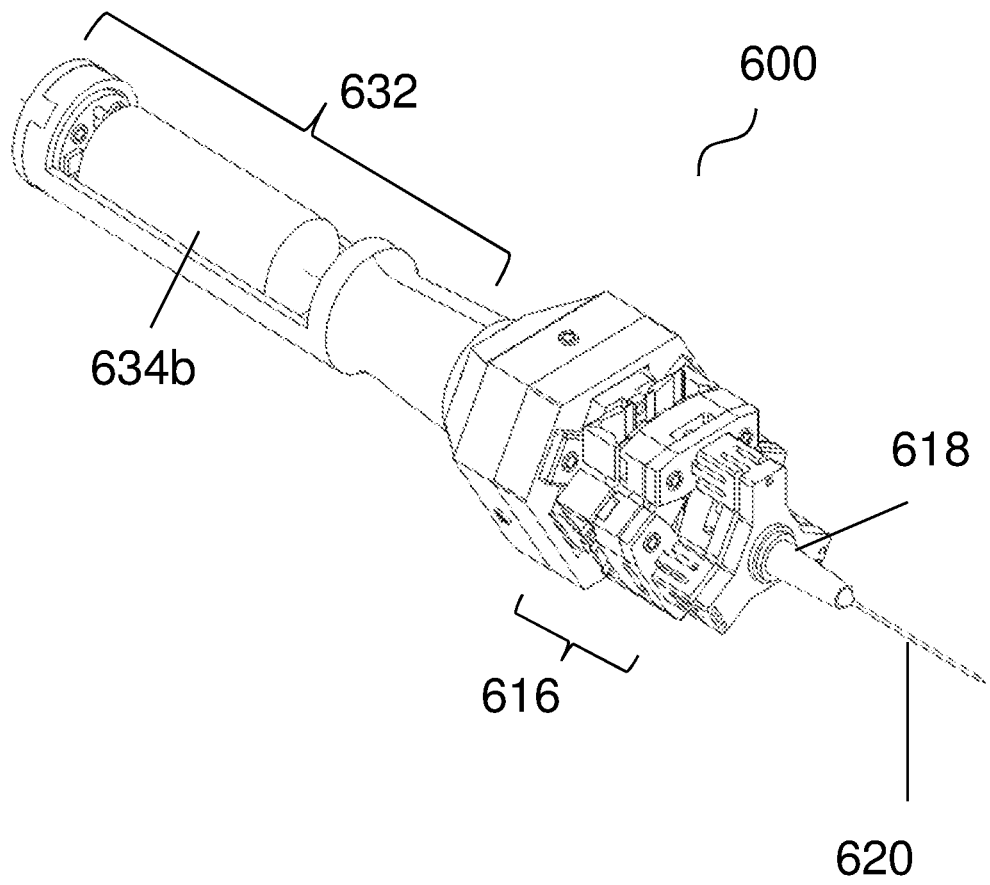
FIG. 6B shows a view of the handheld instrument according to various embodiments with the power source visible.

FIG. 6A shows an external view of a handheld surgical instrument 600 according to various embodiments. FIG. 6B shows a view of the handheld instrument 600 according to various embodiments with the power source 634b visible. The handheld surgical instrument 600 may include a handheld section 632, which may alternatively be referred to as a handle section or a handgrip section. The handheld section 632 may include a power source cover 634a covering a power source 634b such as a battery. The handheld surgical instrument 600 may include a micromanipulator module 616, which may be alternatively referred to as a tremor/motion cancellation/compensation platform. The micromanipulator module 616 may additionally include an adaptor 618 for holding or attaching a controlled tool tip, implement 620 such as a needle. The controlled tool tip or implement 620 may also be referred to as a surgical tool attachment.

Figure 6C:
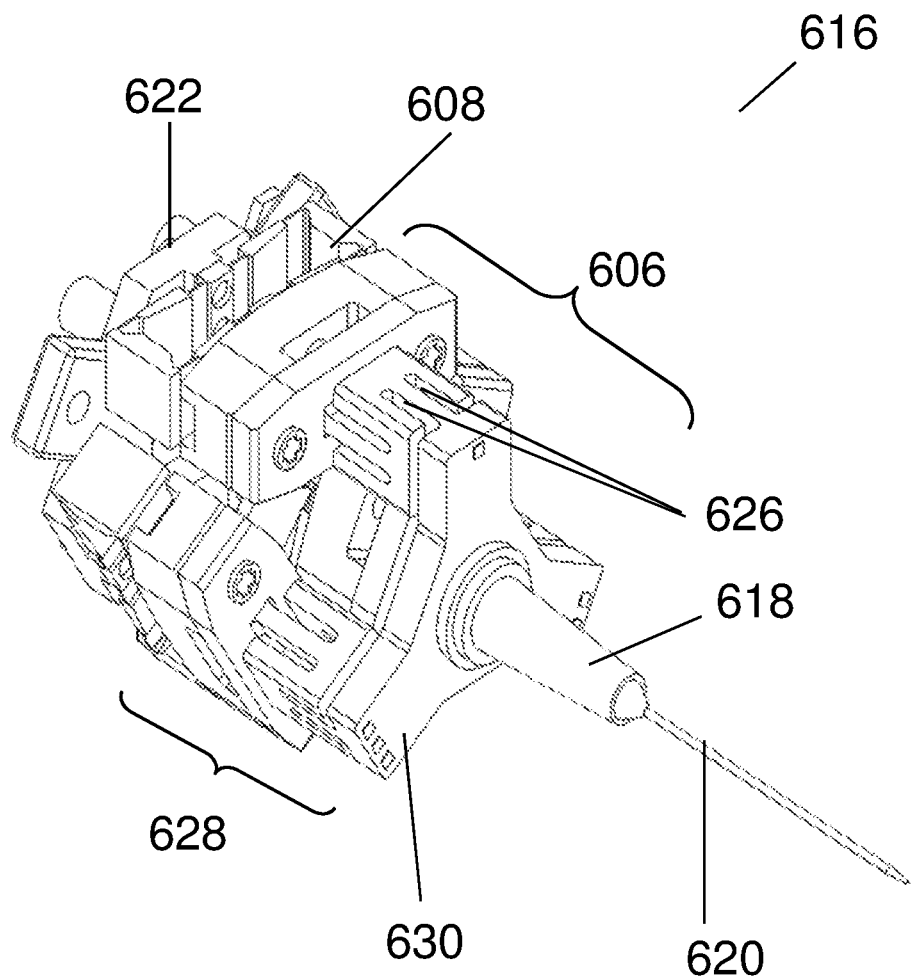
FIG. 6C shows a view of the micromanipulator module according to various embodiments.

FIG. 6C shows a view of the micromanipulator module 616 according to various embodiments. The micromanipulator module 616 may include a fixed base platform 622 attached or fixed to the handle section 632. The micromanipulator module 616 may also include a piezoelectric actuator 608 having a first surface mechanically coupled to the fixed based platform 622. A second surface opposite the first surface of the piezoelectric actuator 608 may be coupled to a movable platform 606. The movable platform 606 may include pivot flexure joints 626, extensible articulated links 628, and movable upper platform 630. The controlled tool tip 620 may be fitted onto the adaptor 618. The micromanipulator module 616 may provide a high precision 3 degrees-of-freedom (DOF) mechanism. In various embodiments, the micromanipulator module 616 or movable platform 606 may include 3 geometrically spaced extensible articulated links 628, which may be similar or identical to one another. Each extensible articulated link 628 may have a first end mechanically coupled to the movable upper platform 630 via 2 pivot joints. Each extensible articulated link 628 may also have a second end opposing the first end mechanically coupled to one prismatic joint of the piezoelectric actuator 608. The actuator 608 may include a linear actuator to actuate the prismatic joint of each limb resulting in relative movements between the fixed base platform 622 and the movable upper platform 630. While FIGS. 6A-C show a device with piezoelectric actuators, any suitable linear actuator may be used, including electromagnetic actuator (e.g. motor, voice coil, solenoid etc.), pneumatic actuator, smart materials actuator (SMA), magneto-restrictive actuator, electrostrictive actuator, dielectric elastomer actuator, or electro-active polymer actuator. A piezoelectric actuator may execute the desired movements with sufficient speed, power and precision (in the low micrometer range). By varying the lengths of the extensible articulated links 628, the movable upper platform 630 may be controlled and manipulated.

In the configuration shown, the orientation and reach in the Z direction may be more important than the translation movement in the X direction or Y direction. The orientation may be adjusted up to ±0.49°, while a stroke in the Z direction may have up to 300 µm reach. In other words, there are 2 degrees-of-freedom of rotation about 2 perpendicular axes intersecting at the center of the movable upper platform and forming a horizontal plane, and 1 degree-of-freedom of a vertical translated motion. The displacement along the Z-axis may be caused by actuating the 3 actuators simultaneously. For rotational movements about the X and/or Y axes, at least 2 actuators, if not 3 at a time, may be actuated. The mechanism may provide accurate positioning for long stroke positioning at high operating rate (>5 Hz).

In various embodiments, the masses in motion may be reduced to a minimum. In various embodiments, the movement of parts of the device/mechanism may be such that the total mass may be of the same order as the inertia of the moving parts of the mechanism/device, resulting in a high operating rate. The 3 moving portions of the mechanism/device may act in parallel to increase in the stiffness of the mechanism/device, enabling better repeatability of position even at high speed. The closed kinematic may have the benefits of more rigidity, speed and accuracy, high force capacity for the number of actuators as the actuators are arranged in parallel rather than in series, and/or relatively simpler inverse kinematics which is an advantage in real-time computer online control.

The movable upper platform 630 may be connected to the extensible links by means of a flexure system including 3 pairs of 2 flexure-based revolute joints in series. The pairs may be equally spaced from one another, with an angle of 20° between neighbouring pairs. The pairs may be at a predetermined radius from the center of the movable upper platform 630. Each pair may include a first flexure member defining a first axis of rotation and a second flexure member defining a second axis of rotation. In this regard, the movable upper platform 630 may be coupled to the flexure system to move about a plurality of axes. These ends of the 3 extensible articulated links 628 may be connected to the fixed base platform 630 and may be equally spaced with an angle 120° between neighbouring links. The 3 extensible articulated links 628 may be at a predetermined radius from the center of the fixed base platform 630.

Using flexure-based technology may eliminate or reduce backlash and friction, thereby providing an accurate mechanical foundation for the micromanipulator module 616. Flexure-based technology may also help to overcome the problems of limited precision and repeatability faced by mechanisms that rely on rolling or friction bearings, which may have considerable backlash and friction.

The adapter 618 may be used to attach controlled tool tips or implements 620 such as standard surgical instruments to the movable upper platform 630. The adapter 618 may include a section that can be attached to the movable upper platform 630 and another section that is coupled to the implement 620. Attachment of implements 620 may improve the operation and use of the tremor/motion cancellation/compensation platform. For instance, using detachable implements 620 may facilitate overall sterilization. The implement 620 may be easily and quickly inserted onto the adapter 618, and may be securely held once attached to the movable upper platform 630.

Figure 6D:
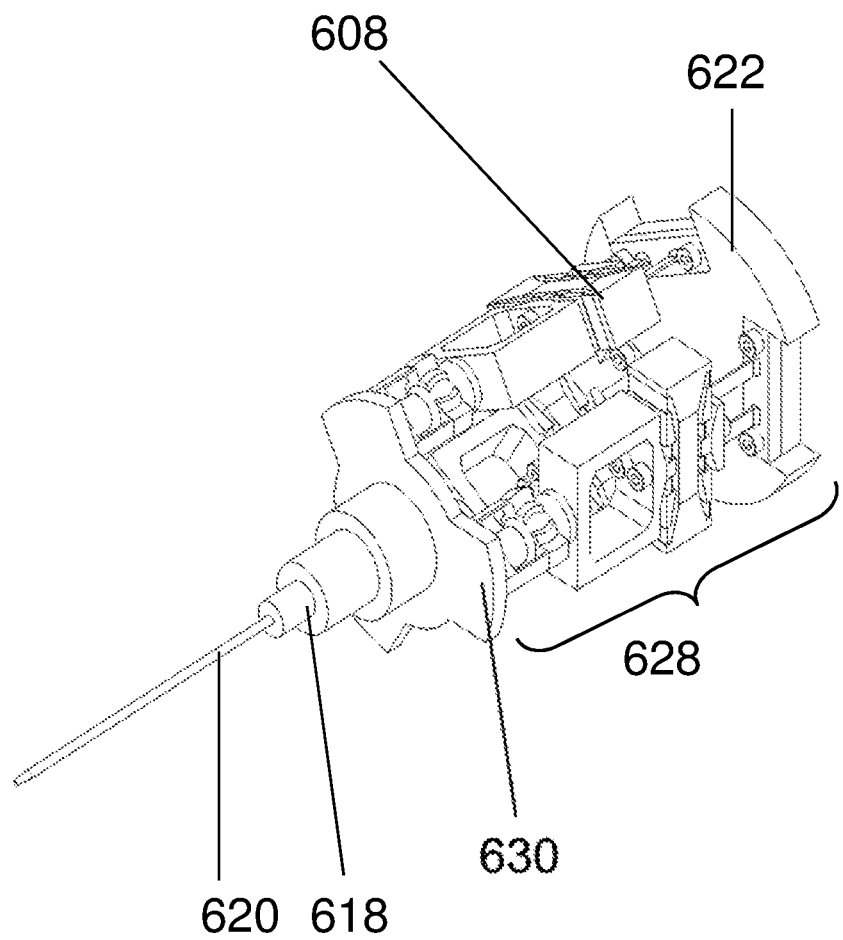
FIG. 6D shows a view of the handheld surgical instrument with a disposable controlled tool tip according to various embodiments.

FIG. 6D shows a view of the handheld surgical instrument with a disposable controlled tool tip 620 according to various embodiments. The instrument 600 may have a sterilizable front end/implement 620, and a non-sterilizable active handle including handle section 612, and micromanipulator module 616. The instrument 600 may be a general surgical tool including a durable/reusable active handle (containing electronics, power source and actuators) and a single-use sterilizable, disposable controlled tool tip or implement 620. The single-use sterilizable, disposable controlled tool tip or implement 620 may be a snap-fit tool to be snapped onto the adapter 618.

The (underactuated) micromanipulator module 616 may include a 3-DOF piezoelectric-driven parallel mechanism including a movable upper surgical tool attachment unit 630 connected to a lower fixed support 622 by 3 identical or similar limbs with symmetrical kinematic structure. The micromanipulator module 616 may control, move and position an end effector 620, such as a tool or element in space, and may enable the control of 3 degrees of freedom using the limbs in parallel, with actuators 608 connected to a fixed support 622, while preserving the parallelism of the moving limbs with respect to the fixed support 622. Each limb may couple the fixed support 622 to the tool attachment 620 by a revolute joint, a prismatic joint (activated by a piezoelectric actuator), and a spherical joint.

Figure 7A:
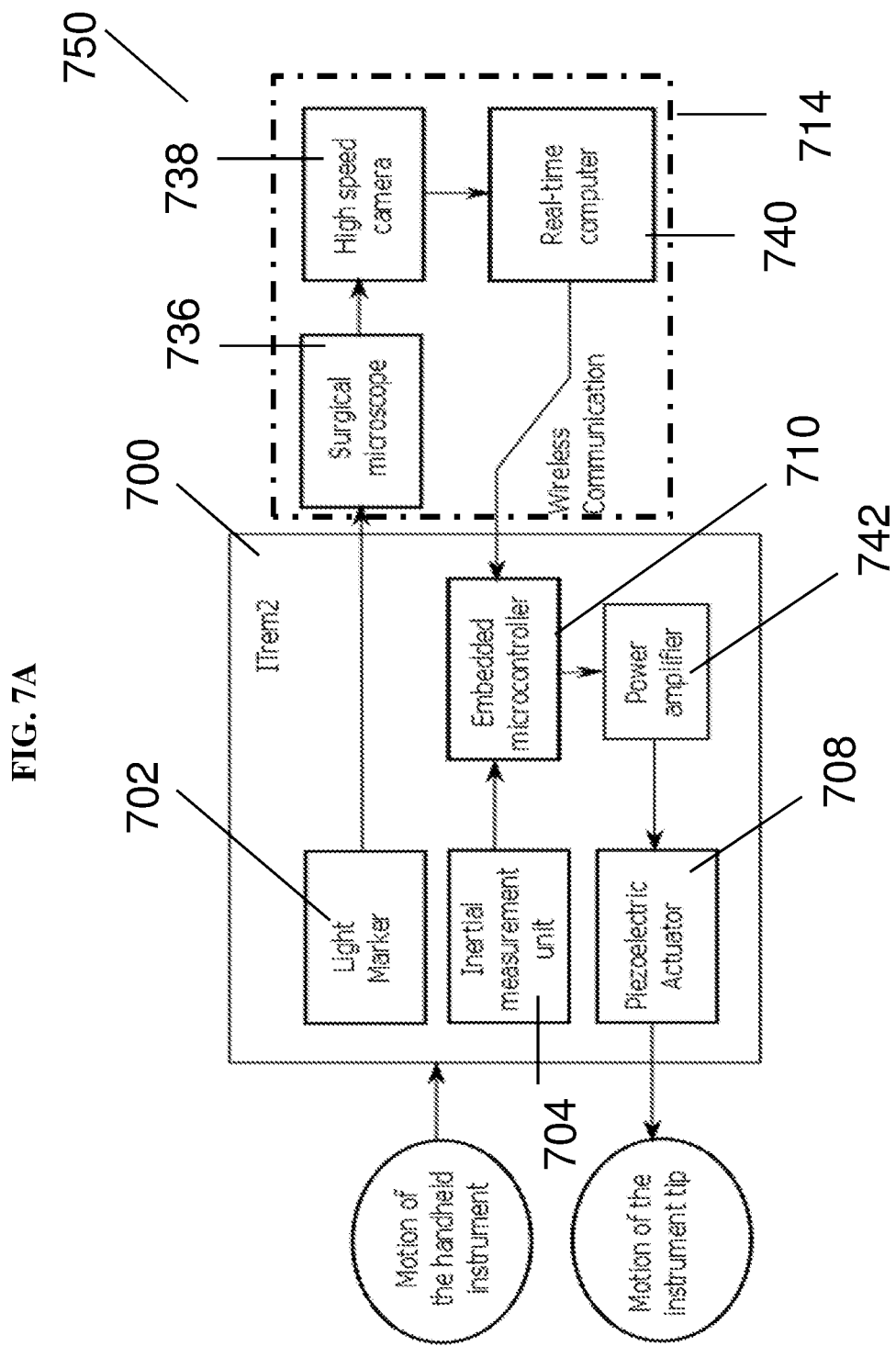
FIG. 7A shows a general illustration of a surgical tool system according to various embodiments.

FIG. 7A shows a general illustration of a surgical tool system 750 according to various embodiments. The surgical tool system 750 may include a handheld surgical instrument 700. The handheld surgical instrument 700 may include a laser source 702, such as a laser diode, configured to emit a laser beam for generating a laser marker on a surface. The handheld surgical instrument 700 may also include an inertial measurement unit (IMU) 704 configured to detect a motion of the handheld surgical instrument 700 and generate a first signal comprising information on the motion of the handheld surgical instrument 700 detected by the inertial measurement unit 704. The handheld surgical instrument 700 may further include an actuator 708, such as a piezoelectric actuator 708, mechanically coupled to a movable platform holding a controlled tool tip. The handheld surgical instrument 700 may additionally include a processing circuit 710, such as an embedded microcontroller, configured to control the actuator 708 to move the movable platform based on the first signal generated by the inertial measurement unit 708 and a second signal.

The surgical tool system 750 may also include a vision unit or sub-system 714, which may also be referred to as a vision module. The vision unit 750 may include a surgical microscope 736 configured to magnify laser marker, and a camera 738 configured to detect the movement of the laser marker by converting an optical signal generated by the laser marker into an electrical signal. The vision unit 750 may further include a computer 740 configured to receive the electrical signal from the camera 738. The computer 740 may be configured to process information comprised in the electrical signal received. The computer 740 may be configured to generate information on the high frequency movement (i.e. at or above a threshold frequency) of the laser marker detected by the vision unit, and the information may be transmitted by the computer 740 or a transmitter coupled to the computer 740 to the processing circuit 710 via a second signal.

As shown in FIG. 7A, the second signal may be transmitted via wireless means. The processing circuit 710 may be configured to control the actuator 708 based on the first signal and the second signal so that the movement of the movable platform holding the controlled tool tip at least partially compensates a tremulous motion of the handheld surgical instrument 700.

The handheld surgical instrument 700 may additionally include a power amplifier 742, which may amplify the output control signal generated by the processing circuit 710 to control the actuator 708.

Figure 7B:
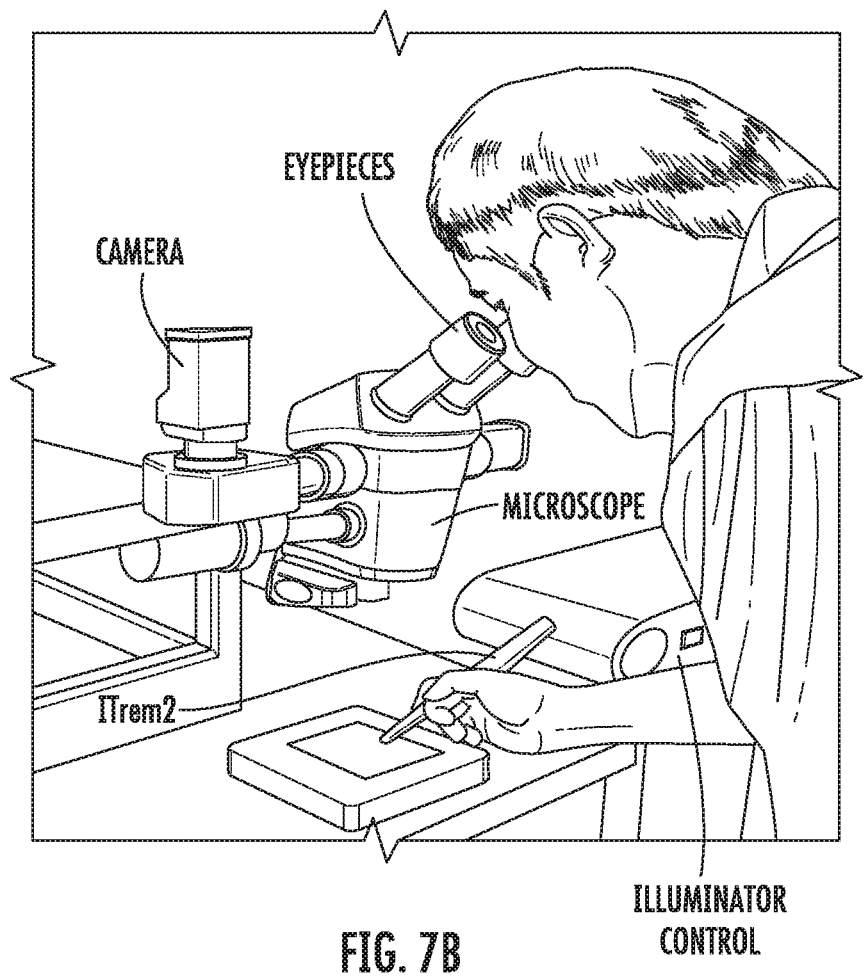
FIG. 7B is an image showing the sensing system in operation according to various embodiments.

The surgical tool system 750 may be referred to as the ITrem2 sensing system, which may be used for microsurgery, while the instrument 700 may be referred to as the ITrem2. FIG. 7B is an image 770 showing the sensing system in operation according to various embodiments. The ITrem2 system may have micrometer scale accuracy, and may also be real-time. The inertial measurement unit (IMU)

704 may include one or more sensors or accelerometers to estimate the movement of the controlled tool tip, and may be non-obtrusive since the sensors or accelerometers may be internally referenced and may be light in weight and mounted inside the instrument body 700. The performance for sensing the movement of the instrument 700 may be enhanced by integrating vision unit 714 with the inertial measurement unit 704. The hand movement of the surgeon including the involuntary components such as tremor and drift may be sensed by the inertial sensors or accelerometers on-board ITrem2. The real-time computer 740 may receive visual inertial information and may estimate the 3 DOF (Degrees of Freedom) controlled tool tip position in real-time. The sensor fusion unit in the embedded microcontroller 710 may improve the position sensing of the controlled tool tip by utilizing accurate time stamps of the real-time computer 740. Time aware fusion of the inertial measurements may provide micrometer accuracy even with significant delay and jitter in the vision measurements.

Microsurgery operations may be normally performed under an optical surgical microscope. Attaching a camera to the microscope may provide the controlled tool tip motion and target position information as seen by surgeon. The surgical microscope 736 may be equipped with a beam-splitter and a stereo attachment for a second observer. The system 750 may allow simultaneous viewing of the workspace by the camera, the surgeon and an assistant. Furthermore, the position information obtained from vision system 714 may not have the problem of drift associated with accelerometers. The vision system 714 may include a high pass filter to filter low frequency drift motion e.g. at about 0-about 1 Hz.

In microsurgery operations, it is important to avoid disastrous movement to any nearby delicate tissue. Therefore, restricting the controlled tool tip from damaging movements is a useful and important automatic visual servoing task. Moreover, there is a need to obtain the absolute position of the controlled tool tip for some automatic visual servoing tasks such as snap-to a target. Sensing of the absolute controlled tool tip position in the world reference frame also opens the door to other improvements such as automatic motion scaling of the controlled tool tip. Because of the notorious drift associated with inertial sensors, there is a problem to detect the absolute world coordinates using the accelerometers only. Microsurgery operations are normally performed under an optical surgical microscope. Attaching a camera to the microscope provides the controlled tool tip motion and target position information as seen by surgeon. A surgical microscope can be equipped with a beamsplitter and a stereo attachment for a second observer. It allows simultaneous viewing of the workspace by the camera, a surgeon and an assistant. Furthermore, the position information obtained from vision system is not drifting.

The vision module 714 may be made up of a table-top optical surgical microscope 736 equipped with a high speed monovision industrial camera 738. A filter with a pass-band that matches to the wavelength of the light source or laser source 702 may be attached to the camera 738 to minimize the interference from ambient light. In order to acquire high quality digital image covering 5 mm×3.7 mm field of view with low noise level, the exposure time may be set to be 5 ms. The sampling rate of the vision unit 714 may be 100 Hz. Real-time image processing may be performed on the real-time embedded computer 740 connected to the camera 738.

The vision unit 714 may acquire the movement information of the instrument body 700 by tracking a reference light marker emitted from a low power (<1 mW) infrared laser diode 702 attached to the instrument body. The movement of the instrument tip without actuation may be referred to as the movement of the neutral tip. The movement of the reference light spot may be considered as the movement of the neural tip as they are attached as one rigid body.

The position of the laser marker may be determined or calculated from the centroid (C) of the laser marker, i.e.:

$$C=[C_X C_Y]^T \qquad (1)$$

where $C_X$ is the x-coordinate of the centroid and $C_Y$ is the y-coordinate of the centroid.

The acquired image may be first converted to binary image by applying a threshold. The resulting image may then be used to mask the original image to calculate the center of energy through the following standard centroid equations:

$$C_X = \frac{\Sigma(x \cdot i(x, y))}{\Sigma i(x, y)} \qquad (2)$$

$$C_Y = \frac{\Sigma(y \cdot i(x, y))}{\Sigma i(x, y)} \qquad (3)$$

where x is the x coordinate of a pixel, y coordinate is the y coordinate of a pixel, and i(x,y) is the intensity value of each pixel.

The vision unit 714 may not only track the movement of the instrument body but may also tracks the ITrem2 controlled tool tip to perform automatic visual servoing tasks. Edge based geometric template matching may be used to track the ITrem2 controlled tool tip because it is capable of locating the template which may be rotated or partially occluded in the image. The template matching may give the position of the controlled tool tip in sub-pixel accuracy.

The high frequency motion component of the laser marker may be used to integrate with the information acquired from the inertial measurement system to estimate the tremulous motion in real-time.

Figure 8A:
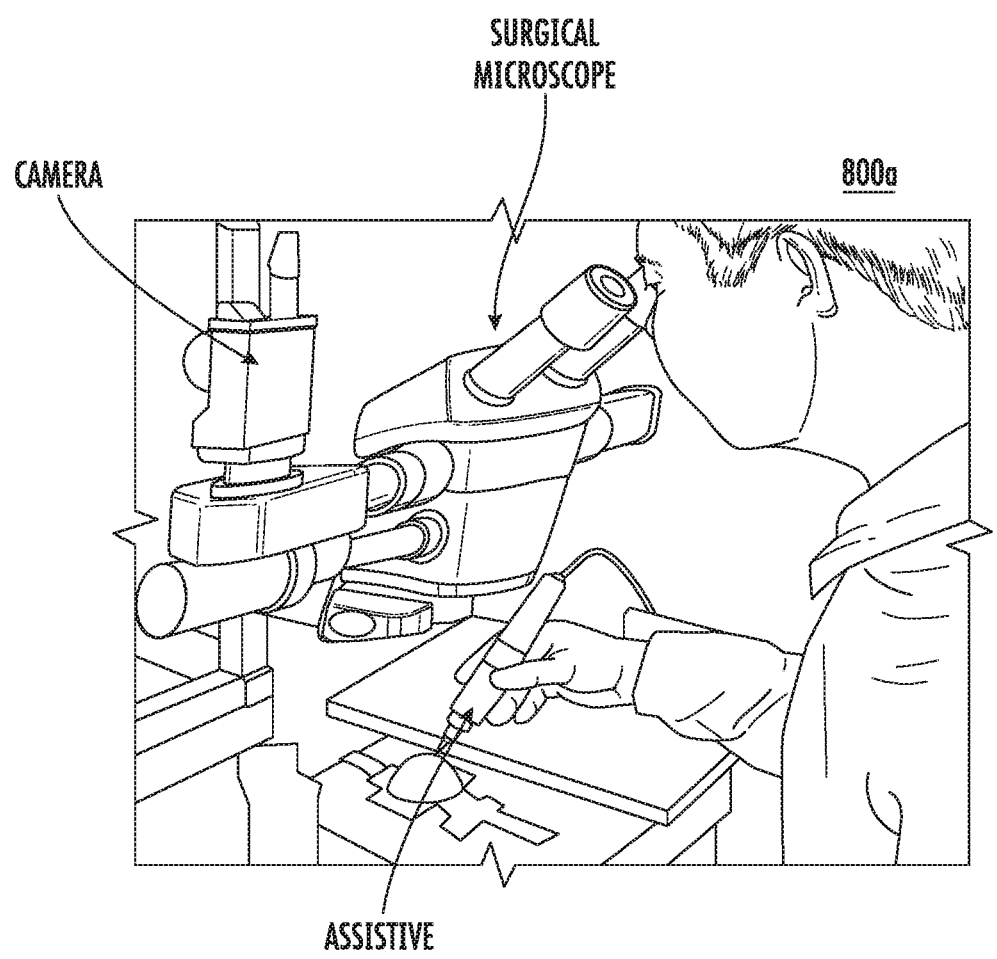
FIG. 8A is an image showing an untrained user being asked to hold the instrument and point at a sharp target tip under a surgical microscope with 25× magnification according to various embodiments.
Figure 8B:
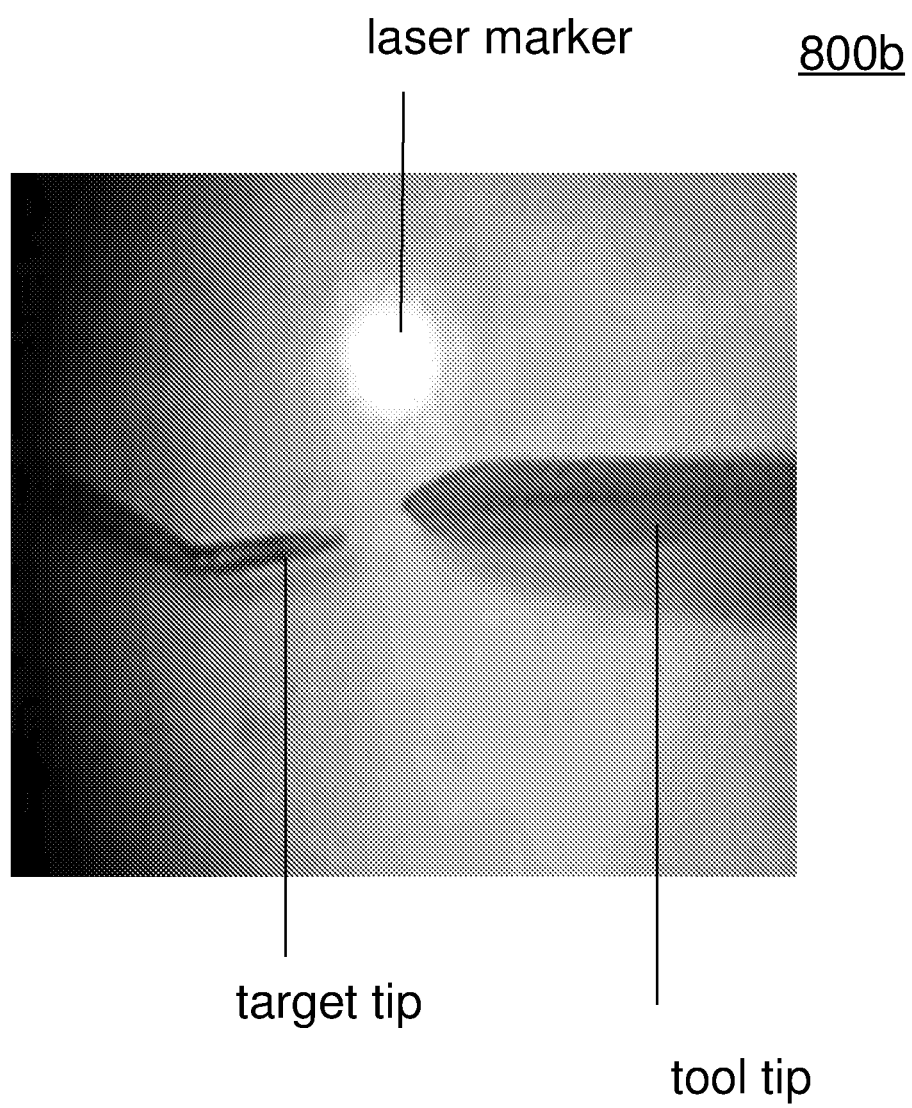
FIG. 8B shows an image of the target tip, the laser marker and the controlled tool tip of the device according to various embodiments.

Handheld experiments may be conducted to evaluate the compensation capability of the assistive instrument. FIG. 8A is an image 800a showing an untrained user being asked to hold the instrument and point at a sharp target tip under a surgical microscope with 25× magnification according to various embodiments. FIG. 8B shows an image 800b of the target tip, the laser marker and the controlled tool tip of the device according to various embodiments.

Figure 9A:
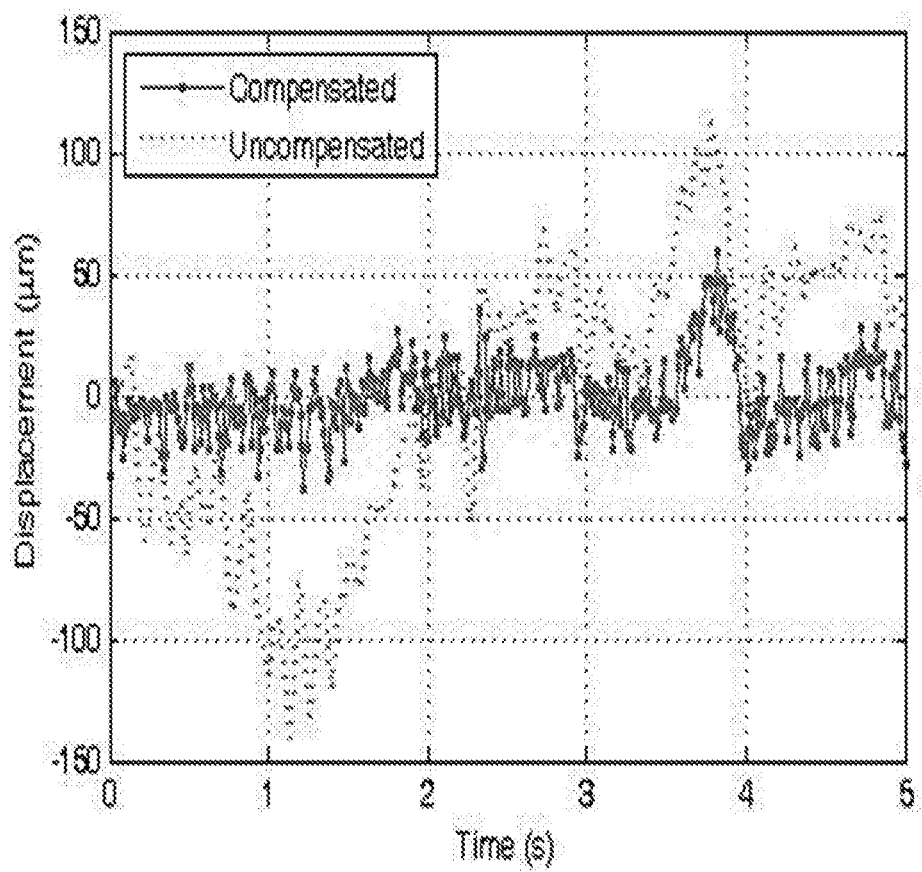
FIG. 9A is a plot of displacement (micrometers or µm) as a function of time (seconds or s) showing the uncompensated movement or displacement of the laser marker and the compensated controlled tool tip displacement according to various embodiments.
Figure 9B:
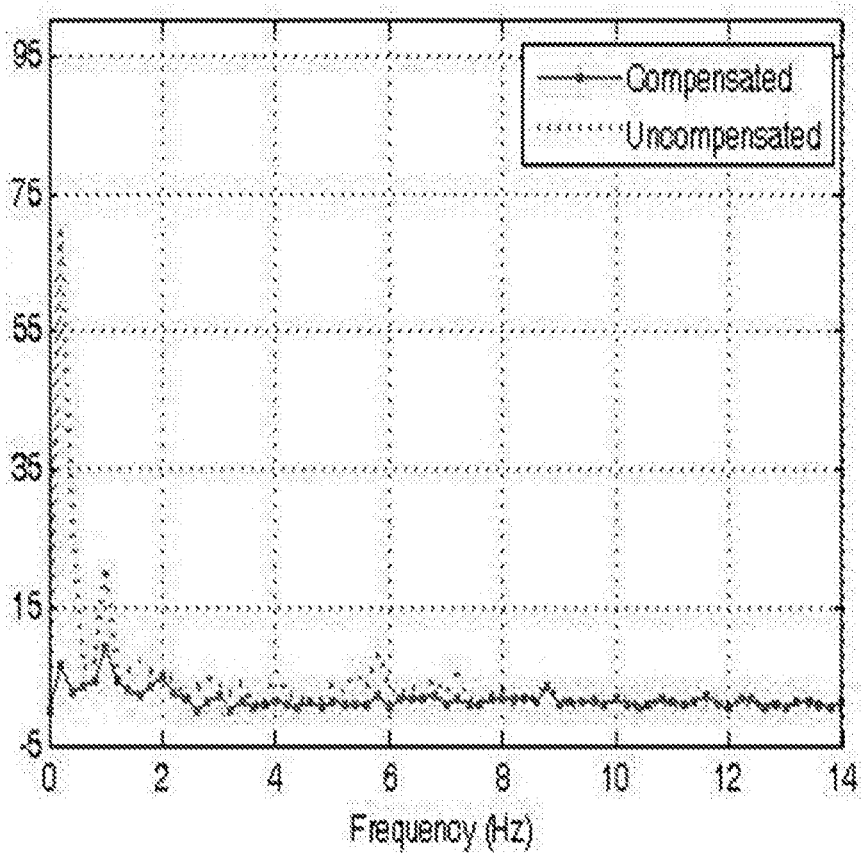
FIG. 9B is a plot of displacement (micrometers or μm) as a function of frequency (hertz or Hz) showing the uncompensated movement or displacement of the laser marker and the compensated controlled tool tip displacement according to various embodiments.

FIG. 9A is a plot 900a of displacement (micrometers or μm) as a function of time (seconds or s) showing the uncompensated movement or displacement of the laser marker and the compensated controlled tool tip displacement according to various embodiments. FIG. 9B is a plot 900b of displacement (micrometers or μm) as a function of frequency (hertz or Hz) showing the uncompensated movement or displacement of the laser marker and the compensated controlled tool tip displacement according to various embodiments. The power of physiological tremor with dominant frequency at 6 Hz and the lower frequency erroneous components (drift & myoclonic jerk) may be visibly attenuated after compensation. If the compensation is perfect, the solid line may be be reduced to random white noise with equal power across all frequencies.

FIG. 9C is a table 900c showing the numerical uncompensated results and the compensated results according to various embodiments.

Figure 10A:
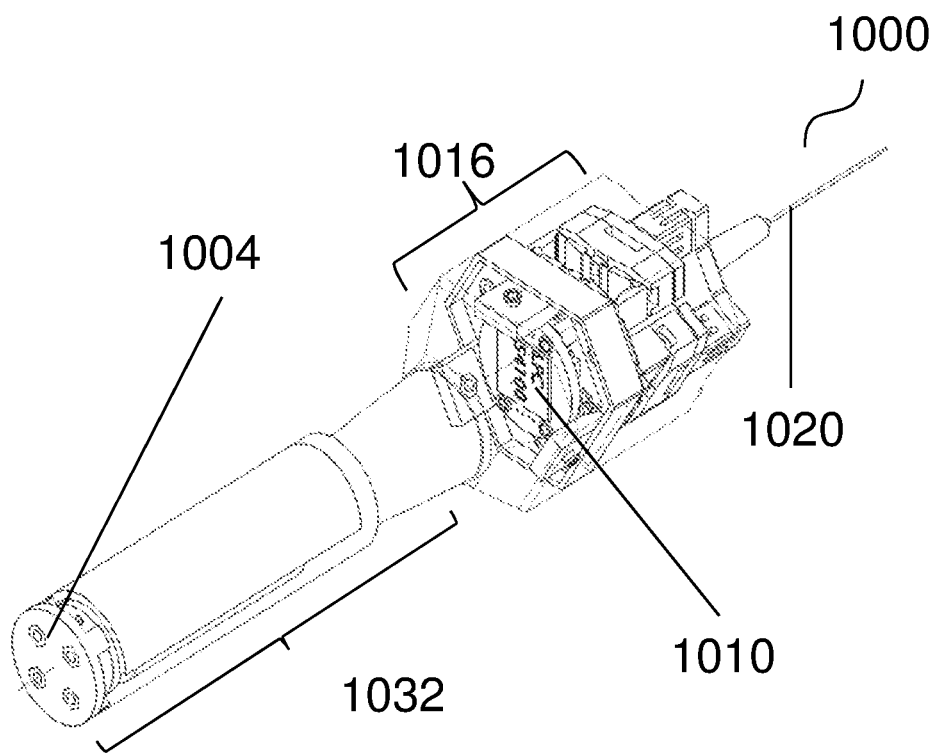
FIG. 10A is a schematic showing a handheld surgical instrument according to various embodiments.

FIG. 10A is a schematic showing a handheld surgical instrument 1000 according to various embodiments. The instrument 1000 may include one or more accelerometers 1004 comprised in the inertial measurement unit. The instrument 1000 may also include a microcontroller 1010 as shown in FIG. 10A. The instrument 1000 may additionally include a handheld section 1032 and a micromanipulator module 1016, which may include an adaptor for holding controlled tool tip 1020.

In various embodiments, there may be four dual-axis digital miniaturized microelectromechanical systems (MEMs) accelerometers 1004 arranged inside the instrument 1000 (ITrem2). The accelerometers 1004 may be configured to sense 3 DOF motion of the controlled tool tip, and 2 DOF orientation of the instrument. The microcontroller 1010 may be configured to perform a moving average filtering and also use a sensor fusion algorithm in real-time to estimate the position of the tip 1020. The real-time computer and the microcontroller 1010 may communicate via wireless communications, such as Zigbee. Zigbee wireless communications may be conducted with a bandwidth of 250 kps for robust and real time communications.

Figure 10B:
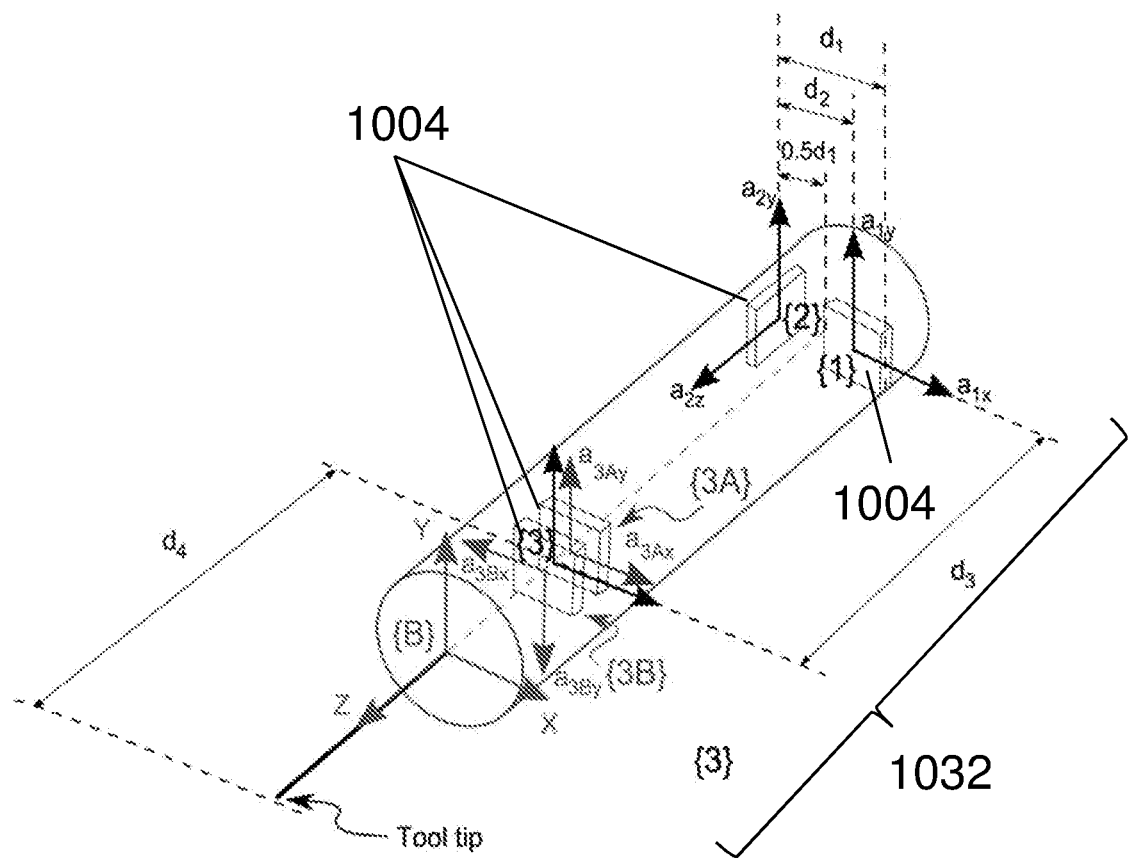
FIG. 10B is a schematic showing the placement of accelerometers in the handheld section according to various embodiments.

The location and orientation of the inertial sensors 1004 may be important in order to achieve high sensing resolution. The accelerometers 1004 may be placed in a long cylindrical space in the instrument body as shown in FIG. 10A but the point of interest to sense the motion is at the needle tip 1020 where it may not be possible to place the accelerometers 1004. FIG. 10B is a schematic showing the placement of accelerometers in the handheld section 1032 according to various embodiments.

The X component and the Y component of accelerometer reading and noise may be magnified more compared to the Z component when converting into the controlled tool tip accelerations. Hence, it may be more beneficial to improve acceleration sensing along X-axis and Y-axis of the body reference frame. On the other hand, the costs of digital MEMS accelerometers may become very low and affordable, whilst their sizes have become very small.

The use of redundant sensors may provide better inertial sensing resolution. However, there may be some difficulties to overcome in order to use redundant sensors. More accelerometers may require more connections or wires to connect to the receiving signal processor. The resultant design of the handheld instrument may become so bulky that the design is no longer ergonomic. More analog-to-digital converters may be required to interface with analogue accelerometers.

In various embodiments, the instrument may be able to attain the advantage of redundancy by deploying or including the embedded microcontroller 1010 with digital interface inside the instrument 1000 as the microcontroller 1010 may allow multiplexing of the data into a single pair of wire. The instrument 1000 with the embedded microcontroller 1010 with digital interface may be more robust to noise because the data are transmitted digitally between the microcontroller 1010 and the real time computer. In addition, pre-filtering tasks may be done on the embedded microcontroller 1010 before transmitting the data to the receiving end.

In various embodiments, the instrument 1000 may include redundant accelerometers. The instrument 1000 may further include two dual-axis sensors instead of one at the controlled tool tip side. The sensors marked 3A and 3B may form a differential pair, and the acceleration reading at location {3} may become better in quality, with undesirable noise such as temperature drift, and other common mode noise effectively removed.

FIG. 10C shows a table 1050 comparing the performance of ITrem2 according to various embodiments with MicronII.

The simulation results in FIG. 10C shows that the performance of ITrem2 is better than its predecessor MicronII by 3 times.

The sensor fusion unit may improve the position sensing of the controlled tool tip by utilizing accurate time stamps of the real-time computer. Time aware fusion of the inertial measurements may provide micrometer accuracy even with significant delay and jitter in the vision measurements. The sensor fusion unit may employ or include first in, first out (FIFO) queues that store the latest acceleration measurements from the IMU and position measurements from vision unit with their respective time stamps. At each inertial measurement cycle, the controlled tool tip acceleration and the corresponding time stamps may be stored in the acceleration queue.

Figure 11A:
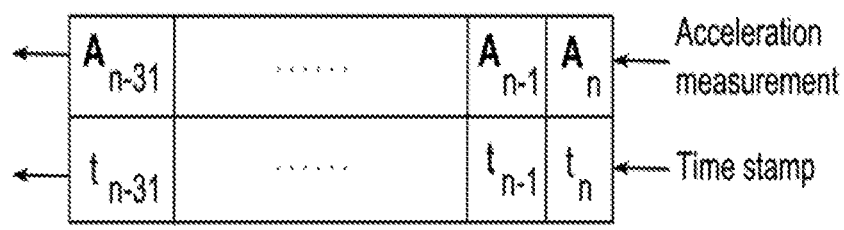
FIG. 11A is a schematic showing the acceleration queue from the inertial measurement unit according to various embodiments.

FIG. 11A is a schematic 1100a showing the acceleration queue from the inertial measurement unit according to various embodiments. The acceleration queue shown in FIG. 11A has 32 elements. During each inertial measurement cycle, the newest acceleration value may be inserted at $A_n$ and the oldest value at $A_{n-31}$ may be discarded.

During each time an image is acquired, the vision unit may store the time stamp of the image with an accuracy of ±1 μs. When the image processing and pose estimation are finished, the estimated position of the neutral tool tip (i.e. the laser marker) in the microscope reference frame, P, and the associated time stamp may be sent to the fusion unit. Since the sampling rate of the vision unit is much slower than that of the inertial measurement, without assuming periodicity, the fusion unit may check the availability of the vision information at each inertial measurement cycle. If new position information from the vision unit is available, the fusion unit may perform the following steps to estimate the current position.

1. Updating the Position Queue

Figure 11B:
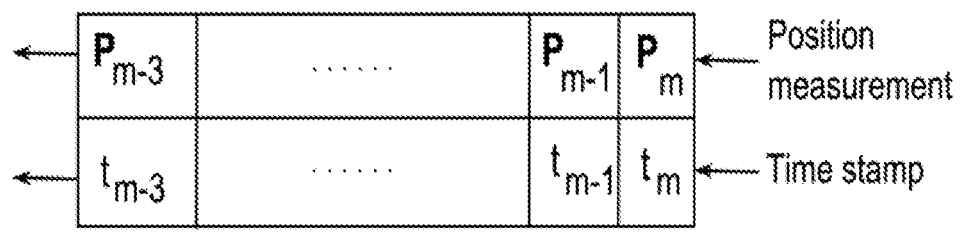
FIG. 11B is a schematic showing the position queue from the vision unit according to various embodiments.

Sampling rate of the inertial measurement unit may be at 333 Hz and that of the vision unit may be at only 100 Hz. At each inertial measurement cycle, the availability of the position information from the vision unit may be checked and FIFO position queue may be updated if the new position measurement is available. FIG. 11B is a schematic 1100b showing the position queue from the vision unit according to various embodiments. FIG. 11B shows the position queue with 4 elements and employing FIFO.

2. Associating the Visual Information and Inertial Information

The position measurements of the neutral tool tip from the vision unit may be associated with the corresponding acceleration measurements in the acceleration queue by checking the time stamps of the images. Due to the considerable jitter in sampling period of the vision unit, delay time of an image may not be constant and the more exact value of the acceleration at a particular time may calculated from the time stamp associated with the image in the position queue.

For a position time stamp, $t_m$ in the position queue, a corresponding new entry may be inserted in the acceleration queue just after the latest time stamp which is earlier than or equal to $t_m$. The time stamp for the corresponding new entry may be denoted as $t_{n-K}$ whose value is about the same as $t_m$ and which satisfies the following relation.

$$t_{n-K-1} \le t_{n-K} < t_{n-K+1} \qquad (4)$$

The acceleration value for the entry, $A_{n-K}$ may be estimated using linear interpolation.

$$A_{n-K} = \frac{t_{n-K+1} - t_{n-K}}{t_{n-K+1} - t_{n-K-1}} A_{n-K-1} + \frac{t_{n-K} - t_{n-K-1}}{t_{n-K+1} - t_{n-K-1}} A_{n-K+1} \quad (5)$$

Similarly, for the position time stamp, $t_{m-1}$ in the position queue, another corresponding entry with time stamp, $t_{n-L}$, and acceleration, $A_{n-L}$ may be inserted in the acceleration queue.

Figure 11C:
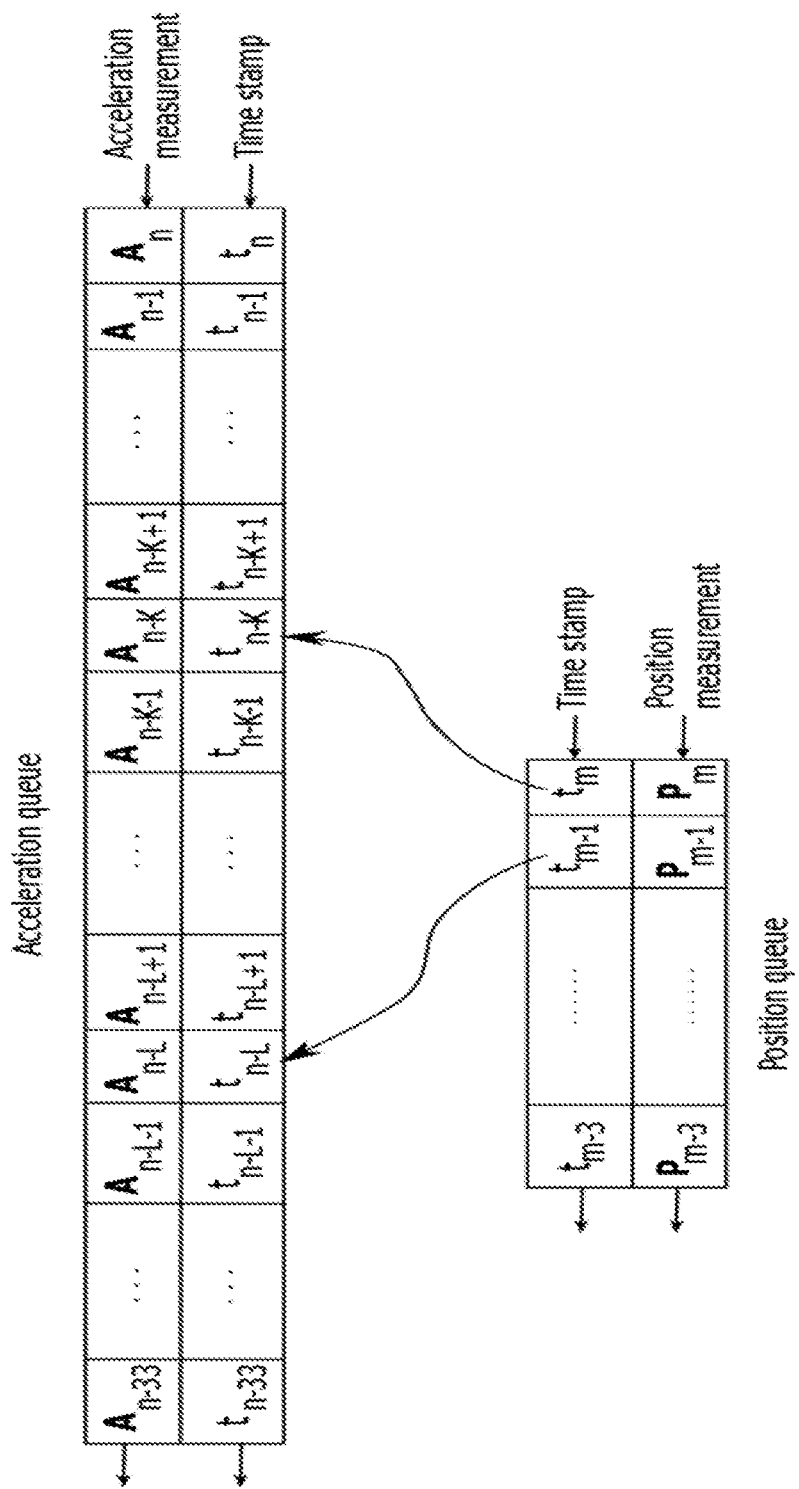
FIG. 11C is a schematic showing the updated acceleration queue from the inertial measurement unit according to various embodiments.

FIG. 11C is a schematic 1100c showing the updated acceleration queue from the inertial measurement unit according to various embodiments. The time stamp, $t_{n-K}$, may be equal to $t_m$. Similarly, $t_{n-L}$ may be equal to $t_{m-1}$.

3. Calculating the Tool Tip Velocity

Figure 11D:
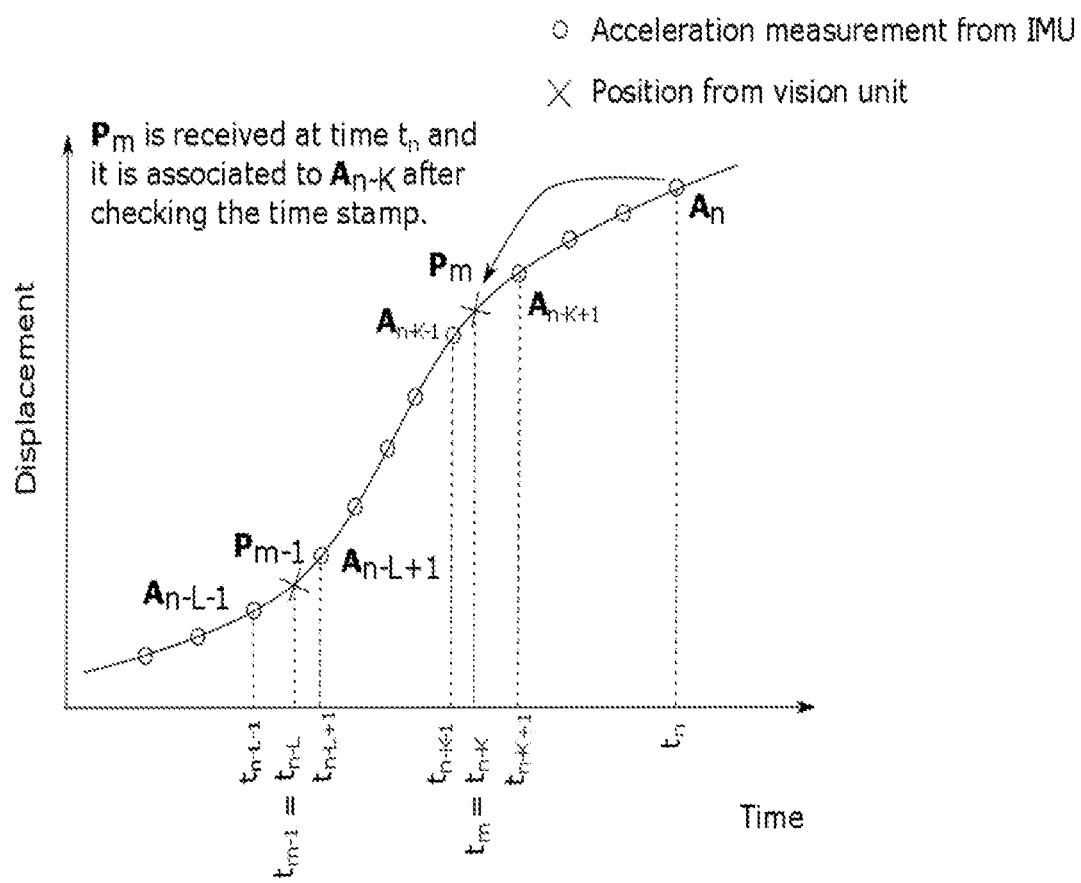
FIG. 11D is a plot of displacement as a function of time showing merging of the acceleration information and vision information according to various embodiments.

The tool tip velocity of the instrument may be calculated using the two positions obtained from vision measurements and the acceleration measurements. FIG. 11D is a plot 1000d of displacement as a function of time showing merging of the acceleration information and vision information according to various embodiments.

Velocity change at $t_{n-L}$ ($\Delta$Vn−L) may be initialized as 0 and the velocity change $\Delta V_i$ at each successive sample point is represented by $$\Delta V_i = \sum_{j=n-L+1}^{i} \frac{A_j + A_{j-1}}{2}(t_j - t_{j-1}), i = n - L + 1, \ldots, n - K. \quad (6)$$

Thereafter, the tool tip position and the velocity estimation at $t_{n-K}$ may be obtained from the following equations.

$$P_{n-K} = P_m \quad (7)$$

$$V_{n-K} = \frac{P_{n-K} - P_{n-L} - \sum_{i=n-L+1}^{n-k} \frac{\Delta V_i + \Delta V_{i-1}}{2}(t_i - t_{i-1})}{t_{n-K} - t_{n-L}} + \Delta V_{n-K} \quad (8)$$

Where $P_{n-L} = P_{m-1}$.

4. Calculating the Tool Tip Position

The tool tip position at time $t_n$ may be estimated from calculated velocity—$V_{n-K}$, position information from vision system—$P_{n-K}$, and acceleration measurements as shown in the following equations.

$$V_i = V_{n-K} + \sum_{j=n-K+1}^{i} \frac{A_j + A_{j-1}}{2}(t_j - t_{j-1}), \quad (9)$$

$$i = n - K + 1, \ldots, n.$$

The estimated tool tip position at time $t_n$ is denoted by $P_n$.

$$P_n = P_{n-K} + \sum_{i=n-K+1}^{n} \frac{V_i + V_{i-1}}{2}(t_i - t_{i-1}) \quad (10)$$

If there is no new vision information, the fusion unit may simply update the pose estimation for the current acceleration sample value using the above two equations.

After estimating the position for the current sample, the fusion unit may predict the tool tip position in advance to offset the inherent delay associated with the actuation unit. For the prediction time, $\Delta t_p$, the predicted tool tip position, $P_p$, is calculated as follows.

$$P_p = P_n + V_n \times \Delta t_p - \frac{A_n}{2} \times \Delta t_p^2 \quad (11)$$

In various embodiments, the instrument may be designed to have a universal adapter compatible with current surgical tools. Various controlled tool tips may be fitted with the adapter. In various embodiments, four types of controlled tool tips may be engineered to incorporate the most common surgical tools used during a microsurgery.

The tip of the assisted handheld instrument may be designed to be replaceable and disposable. Currently, four types of tips are under development, including micro-forceps, micro-needle holder, micro-scissors and micro-surgical needle/blade. The replaceable feature (Snap-On style) may allow surgeons to switch the surgical tips easily for various applications. The disposable feature may simplify the sterilization procedure.

Figure 12A:
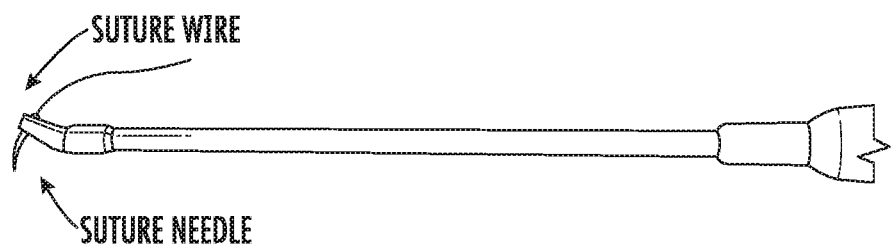
FIG. 12A is an image of a micro-needle holder according to various embodiments holding a suture needle.
Figure 12B:
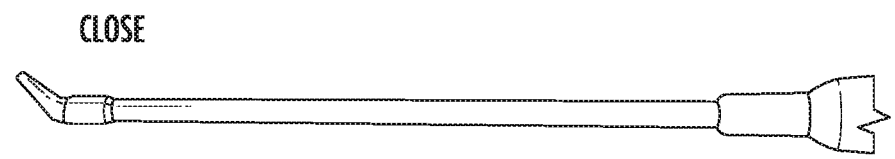
FIG. 12B is an image of the micro-needle holder according to various embodiments in a closed arrangement.
Figure 12C:
FIG. 12C is an image of the micro-needle holder according to various embodiments in an open arrangement.
Figure 12D:
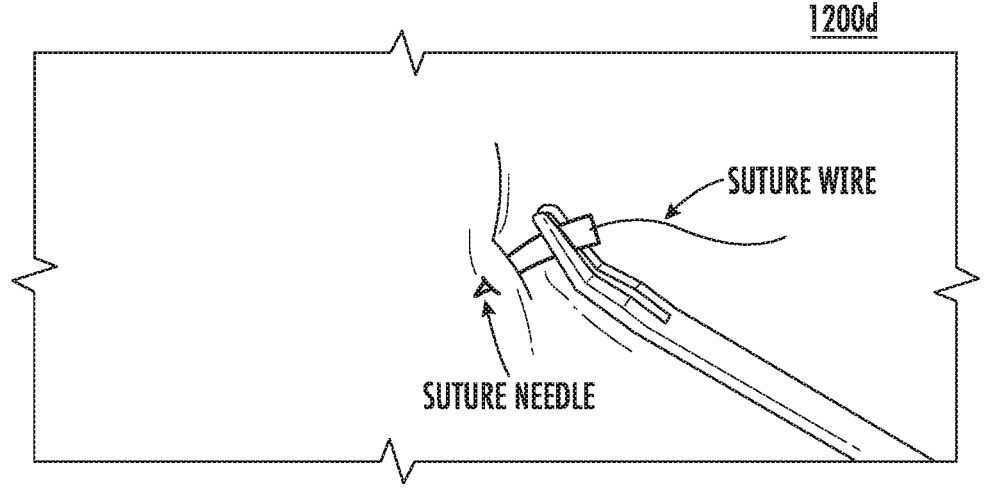
FIG. 12D is an image of the micro-needle holder according to various embodiments holding the suture needle during operation.

FIG. 12A is an image 1200a of a micro-needle holder according to various embodiments holding a suture needle. FIG. 12B is an image 1200b of the micro-needle holder according to various embodiments in a closed arrangement. FIG. 12C is an image 1200c of the micro-needle holder according to various embodiments in an open arrangement. FIG. 12D is an image 1200d of the micro-needle holder according to various embodiments holding the suture needle during operation.

Figure 12E:
FIG. 12E is an image of a micro-scissors according to various embodiments in closed arrangement.
Figure 12F:
FIG. 12F is an image of the micro-scissors according to various embodiments in closed arrangement.

FIG. 12E is an image 1200e of a micro-scissors according to various embodiments in closed arrangement. FIG. 12F is an image 1200f of the micro-scissors according to various embodiments in closed arrangement.

The controlled tool tip may be driven by electromagnets. The instrument may include one or more electromagnets, which are able to generate 1.5 N grabbing/cutting force to hold the suture needle and to cut the blood vessel or tissue. The maximum opening width of the needle holder may be about 1.5 mm, which allows easy pick-ups of various suture needles, from size 6/0 to 12/0. The maximum opening width of the scissors may be designed to be about 1.2 mm, which is sufficient for cutting different types of tissues.

The controlled tool tips may include radio-frequency identification (RFID) chip for authentication purpose. The RFID may contain information such as the authentication detail, the usage record, the regional information, the type of the controlled tool tip, etc.

To increase the ease of use of the hand-held instrument, a separate installation device may be designed to authenticate and install the controlled tool tip onto the hand-held device. The installation device may be further configured to perform calibration of the system.

The installation device may be able to read the RFID chip embedded in the controlled tool tip. The installation device may be configured so that the installation device only performs the installation of the controlled tool tip according to its type only if the device confirms the controlled tool tip is genuine, is used for the first time, and is planned to be sold in this specific region. Once the controlled tool tip is secured on the hand-held instrument, the device may perform calibration automatically. The entire process may take less than 30 seconds.

There is a clear need for technology assisted solutions in applications which require manual micromanipulation that pushes human sensory-motor limits, especially in the surgical space. Not only does the instrument/system hold the promise of better clinical outcome for many existing microsurgical interventions, various embodiments may also make possible certain procedures which are currently deemed impossible to perform.

The assistive handheld microsurgical instrument may be intended to be introduced as a general surgical tool comprising a durable/reusable active handle (containing electronics, power, and actuators) with a single-use sterilizable, disposable surgical tool attachment.

Various embodiments may provide a system and/or a method that adopts a less obtrusive, lowers cost, maximizes ease of use, user acceptance, and/or is compatible with current surgical practice with respect to accuracy enhancement. Various embodiments may provide a completely portable hand-held tool, with the instrument size and weight as close as possible to that of existing passive instruments. The assistive handheld microsurgical instrument may be a self-contained untethered instrument with a detachable and sterilizable single-use surgical tool attachment. The instrument may be configured to sense its own motion via non-contact sensing by using on-board inertial sensors, distinguish between erroneous motion and intended motion of the hand with real-time filtering and sensor fusion algorithms, and compensate the erroneous component by deflecting the controlled tool tip in an equal but opposite motion in real-time with a robotic micromanipulator.

Computer vision techniques may further enhance the positioning accuracy of the instrument and may extend its capability to execute vision-guided surgical intervention by making use of images from a microscope mounted camera.

Various embodiments may relate to the untethered handheld instrument mechanism design, design of the disposable tip, sensing system using light marker, placement configuration of inertial sensors, and/or clamping tip design.

In various embodiments, the instrument may include a laser source such as an infrared (IR) light emitting diode (LED) to generate two parallel IR laser beams. Two laser markers may be formed on the surface, which may be captured by an IR camera. Tilt angles with respect to the X-axis and Z-axis of the instrument may be generated from the inertial measurement unit (IMU). A pan angle rotation of the instrument may be determined or calculated by using the tilt angle and orientation of the two laser markers.

The two markers formed by the two parallel infrared (IR) laser beams produced by the IR LED may be captured by the monocular IR camera fastened or attached to a microscope. The centroids of the two laser markers may be denoted by $C_0$ and $C_1$. The light reference plane $\{L\}$ may be the coordinate frame whose X- and Y-axis are on the focal plane. The origin of $\{L\}$ may be at $C_0$. The coordinate frame of the instrument body may be defined as the body reference frame $\{B\}$.

Figure 13A:
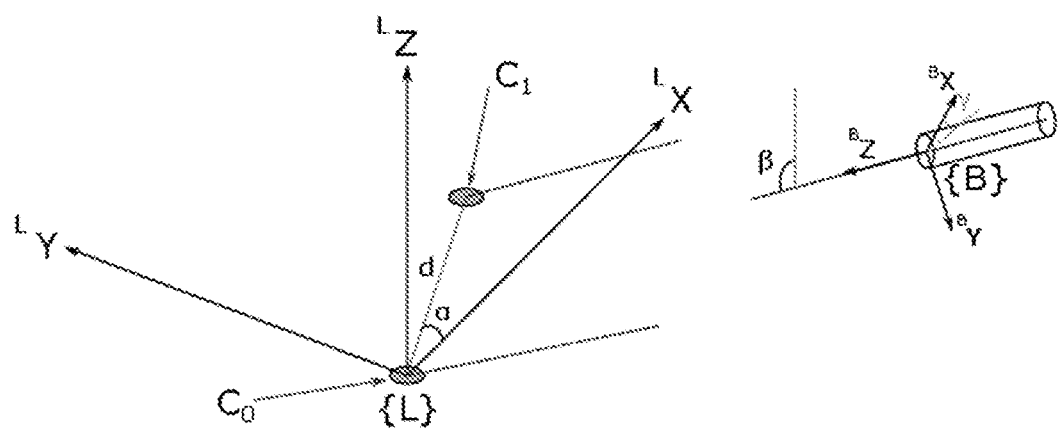
FIG. 13A is a schematic illustrating the definitions of the reference frames of the light reference frame and the reference frame of the instrument body according to various embodiments as well as the associated rotations angles.

FIG. 13A is a schematic 1300a illustrating the definitions of the reference frames of the light reference frame and the reference frame of the instrument body according to various embodiments as well as the associated rotations angles. The distance between the centroids of the two laser markers may be denoted as d. The pan angle rotation of the instrument body with respect to the Z-axis of the light reference frame $\{L\}$ may be denoted as $\alpha$. The tilt angle denoted as $\beta$ may be defined as the angle between the Z-axis of the light reference frame $\{L\}$ and the Z-axis of the body reference frame $\{B\}$. The roll able of the instrument body with respect to the Z-axis of the body reference frame $\{B\}$ may be defined as $\gamma$.

Figure 13B:
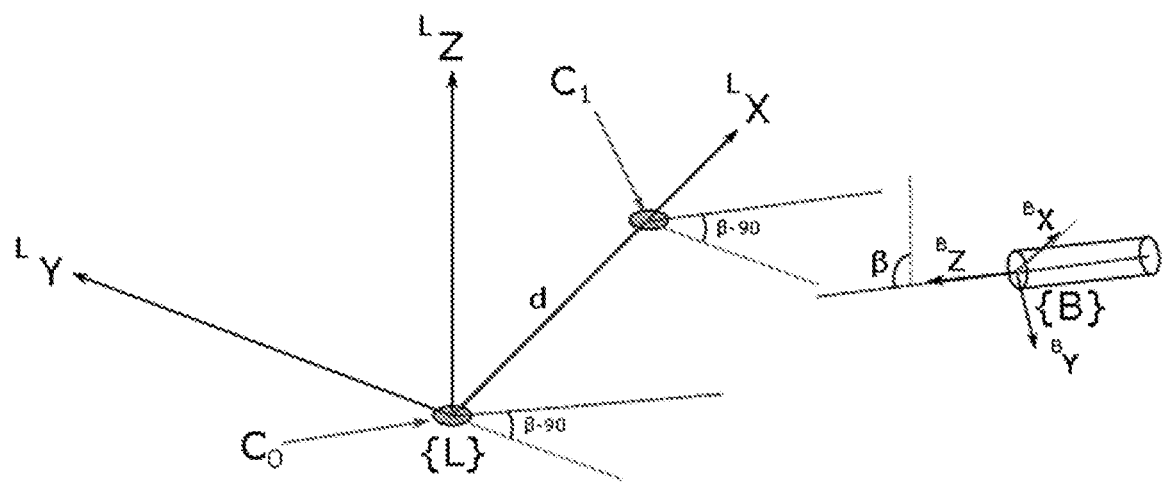
FIG. 13B is a schematic showing the centroid of the first laser marker $C_0$ and the centroid of the second laser marker $C_1$ on the X-axis of the light reference frame $\{L\}$.

FIG. 13B is a schematic 1300b showing the centroid of the first laser marker $C_0$ and the centroid of the second laser marker $C_1$ on the X-axis of the light reference frame $\{L\}$. The pan angle $\alpha$ and roll angle $\gamma$ may be defined as zero when $C_0$ and $C_1$ are on the X-axis of the light reference frame $\{L\}$. In this condition, the variation in $\beta$ may not affect the positions of the laser markers in $\{L\}$.

Figure 13C:
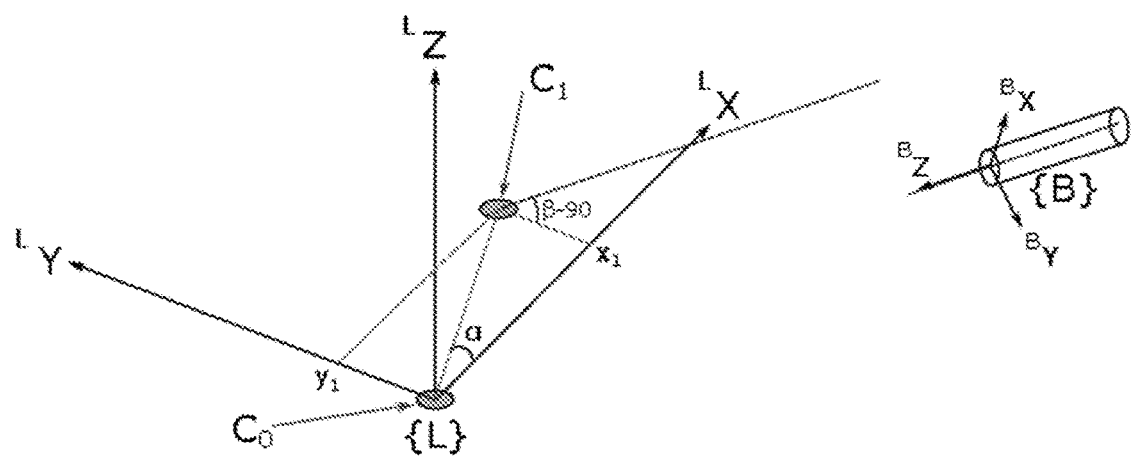
FIG. 13C is a schematic showing the roll angle γ at zero.

FIG. 13C is a schematic 1300c showing the roll angle $\gamma$ at zero. When the roll angle $\gamma$ is zero, the pan angle $\alpha$ may be the same as the angular movements of $C_1$. If the coordinates of $C_1$ are $\{x_1, y_1\}$, the pan angle $\alpha$ may be provided by:

$$\alpha = \tan^{-1} \frac{y_1}{x_1} \tag{12}$$

When $\gamma=0$, the tilt angle may not affect the value of the pan angle.

Figure 13D:
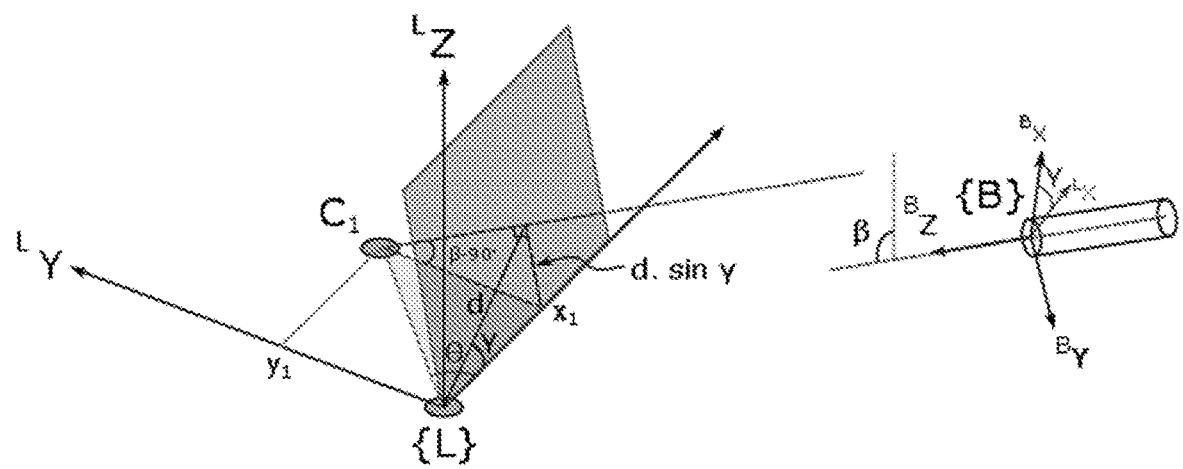
FIG. 13D is a schematic showing the effect of the tilt angle and roll angle on the centroid of the second laser marker $C_1$.

FIG. 13D is a schematic 1300d showing the effect of the tilt angle and roll angle on the centroid of the second laser marker $C_1$. When the pan angle $\alpha$ is zero, the coordinates of $C_1$ may depend on the roll angle $\gamma$, and the tilt angle $\beta$. The length of the line segment which connects to the point $(x_1, 0)$ from $C_1$ normally may be provided as $d.\sin\gamma$. It follows that $$x_1 = d \cdot \cos\gamma \tag{13}$$

and $$y_1 = \frac{d \cdot \sin\gamma}{\sin(\beta - 90°)} \tag{14}$$

The angle $\theta$ due to tilt and roll may be provided as:

$$\tan\theta = \frac{y_1}{x_1} \tag{15}$$

$$\tan\theta = \frac{\frac{d \cdot \sin\gamma}{\sin(\beta - 90°)}}{d \cdot \cos\gamma} \tag{16}$$

Therefore, $$\theta = \tan^{-1} \frac{\tan\gamma}{\sin(\beta - 90°)} \tag{17}$$

When $\alpha$, $\beta$, and $\gamma$ are not zero, the orientation of the laser markers $\phi$ may be provided by:

$$\phi = \tan^{-1} \frac{y_1}{x_1} \tag{18}$$

Further, $$\phi = \alpha + \theta \tag{19}$$

Therefore, the value of the pan angle may be provided by:

$$\alpha = \tan^{-1} \frac{y_1}{x_1} - \tan^{-1} \frac{\tan\gamma}{\sin(\beta - 90°)} \tag{20}$$

For two laser markers with centroids at $(x_0, y_0)$ and $(x_1, y_1)$, the pan angle $\alpha$ may be calculated by using the tilt angle $\beta$ and the roll angle $\gamma$ as provided:

$$\alpha = \tan^{-1}\frac{y_1 - y_0}{x_1 - x_0} - \tan^{-1}\frac{\tan\gamma}{\sin(\beta - 90°)} \quad (21)$$

When $\phi$ is greater than 45°, exchanging the numerator and denominator to compute 90°−$\phi$ should provide a more accurate result for the first term.

For the second term, when $\beta$ is near 90°, the resolution may be lower. In other words, then the instrument is almost horizontal, a small change in tilt may result in a large movement of the laser markers on the surface.

Regarding the roll angle $\gamma$ in the second term, the closer the roll angle to 90°, the lesser the effect of $\beta$ on the results. When the roll angle is 90°, the tilt angle $\beta$ may have no effect on the orientation of the laser markers. A conditional test may be provided on the computer for the roll angle to be about or near 90° to avoid overflow errors.

FIG. 14A is a table 1400a comparing various parameters of the instrument/system according to various embodiments and the Da Vinci System (Tele-operated Surgical Robotics System). The Da Vinci System is from Intuitive Surgical, Inc. Despite successes in other surgical procedures, the adoption rate of the da Vinci surgical system in microsurgery is negligible. The Da Vinci surgical robot in its current form is not ideally suited to microsurgical procedures, in terms of positioning accuracy and tool-tip manipulation dexterity. The approximate fiducial localization error (FLE) of Da Vinci surgery system is 1 mm, whereas the typical maximum error at the controlled tool tip of a microsurgeon is only 0.3 mm.

In the human arm, the surgeon is already in possession of a dexterous manipulator with high bandwidth, and an unbeatable natural user interface. Rather than developing a robotic system that must duplicate many of the human hands' features and introduces disadvantages in terms of naturalness of feel, the philosophy underlying the approach as described herein is to retain the advantages possessed by the human surgeon, and to augment only those aspects that require augmentation—tip positioning accuracy.

Compared to tele-operation, the approach as described herein reduces hardware cost by dispensing with the master interface and the robotic arm, requiring only a micromanipulator for the instrument tip.

The range of the micromanipulator at the instrument tip is designed to be only as much as is needed for compensation of tremor and similar erroneous movements. Safety and liability issues are thus minimized, because even in case of failure the system is not capable of displacing its tip more than a few hundred microns. If the system is shut down, it simply becomes a passive handheld instrument such as the surgeon has worked with for years.

In terms of cost and likelihood of user acceptance, the steady-hand robot from John Hopkins University (JHU) sits between the Da Vinci system and the approach as described herein. The hardware cost of the system according to various embodiments would be less than half of the JHU system. The dexterity of the human hand is also lost in the steady-hand robot, as the tool's movement is constrained by the limited degrees-of-freedom of the robot. The robotic system from JHU has been last reported to be in proof-of-concept phase in June 2013.

FIG. 14B is a table 1400b comparing various parameters of the instrument/system according to various embodiments and the Micron handheld instrument. The Micron handheld instrument is from Carnegie Mellon University (CMU). The CMU device depends on a custom-built PSD (position sensitive detector) based optical tracking system with limited sensing volume (<8 cm$^3$: 2×2×2 cm). The line of sight between the infrared emitters mounted on the CMU device and the PSD must not be interrupted. Such a setup would be impractical for real clinical deployment.

On the other hand, various embodiments may include a combination of on-board accelerometers and a camera attached to the microscope (a standard surgical microscope configuration), which is unobtrusive to the surgeon. The primary function of the device is to dampen the natural hand tremors of the surgeon in 3D space and not to perform the intricacies of microsurgery. To compensate for the small involuntary movements at the tool-tip, only 3 DOF is needed. The tool-tip may not have pitch and yaw movement during microsurgery, any pitch and yaw movement produced by the surgeon's hand may be almost equivalent to pure translation at the tool-tip. There may be almost no detectable tremulous error in the roll DOF. Hence, in term of tremor compensation at the tool-tip, a 6 DOF device may not have any advantage at all.

There is no commercialization plan for the Micron handheld instrument.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

The invention claimed is:

1. A handheld surgical instrument comprising:
    a laser source configured to emit a laser beam so that a laser marker is generated on a surface;
    an inertial measurement unit configured to detect a motion of the handheld surgical instrument and generate a first signal comprising information on the motion of the handheld surgical instrument detected by the inertial measurement unit;
    a movable platform for holding a controlled tool tip;
    an actuator mechanically coupled to the movable platform; and
    a processing circuit configured to control the actuator to move the movable platform based on the first signal generated by the inertial measurement unit and a second signal generated by a vision unit based on a movement of the laser marker, so that the movement of the movable platform holding the controlled tool tip at least partially compensates a tremulous motion of the handheld surgical instrument.

2. The handheld surgical instrument according to claim 1, wherein the laser beam comprises visible light or infrared light.

3. The handheld surgical instrument according to claim 1,
    wherein the handheld surgical instrument further comprises a beam splitter configured to separate the laser beam to form the laser marker and a further laser marker on the surface; and
    wherein the second signal is generated by the vision unit based on the movement of the laser marker and a movement of the further laser marker.

4. The handheld surgical instrument according to claim 1, wherein the laser marker is of any shape selected from a group consisting of a circular shape, a rectangular shape, a T-shape, and a cross shape.

5. The handheld surgical instrument according to claim 1, wherein the inertial measurement unit comprises one or more accelerometers for detecting the motion of the handheld surgical instrument.

6. The handheld surgical instrument according to claim 1,
wherein the first signal comprises information on the motion of the handheld surgical instrument within a range of frequencies including a frequency of intended motion of the surgical instrument; and
wherein the second signal comprises information on the movement of the laser marker above a predetermined threshold, the predetermined threshold set above the frequency of intended motion of the surgical instrument.

7. The handheld surgical instrument according to claim 6, wherein the processing circuit is configured to control the actuator to move the movable platform based on the first signal and the second signal so that the intended motion of the surgical instrument is uncompensated by the movement of the movable platform.

8. A surgical tool system comprising:
a handheld surgical instrument comprising:
a laser source configured to emit a laser beam so that a laser marker is generated on a surface;
an inertial measurement unit configured to detect a motion of the handheld surgical instrument and generate a first signal comprising information on the motion of the handheld surgical instrument detected by the inertial measurement unit;
a movable platform for holding a controlled tool tip;
an actuator mechanically coupled to the movable platform; and
a processing circuit configured to control the actuator to move the movable platform based on the first signal generated by the inertial measurement unit and a second signal; and
a vision unit configured to detect a movement of the laser marker, and further configured to generate the second signal, the second signal comprising information on the movement of the laser marker detected by the vision unit;
wherein the processing circuit is configured to control the actuator so that the movement of the movable platform holding the controlled tool tip at least partially compensates a tremulous motion of the handheld surgical instrument.

9. The surgical tool system according to claim 8,
wherein the handheld surgical instrument further comprises a beam splitter configured to separate the laser beam to form the laser marker and a further laser marker on the surface; and
wherein the vision unit is configured to detect the movement of the laser marker and a movement of the further laser marker.

10. The surgical tool system according to claim 8, wherein the vision unit comprises a camera configured to detect the movement of the laser marker by converting an optical signal generated by the laser marker into an electrical signal.

11. The surgical tool system according to claim 10, wherein the vision unit further comprises a surgical microscope configured to magnify laser marker.

12. The surgical tool system according to claim 10, wherein the vision unit further comprises a computer configured to receive the electrical signal from the camera;
wherein the computer is further configured to determine a centroid of the laser marker; and
wherein information on the movement of the laser marker is information on a movement of the centroid of the laser marker.

13. The surgical tool system according to claim 12,
wherein the computer is configured to generate and transmit the second signal to the processing circuit of the handheld surgical instrument;
wherein the computer is further configured to filter out the movement of the laser marker at or below a predetermined threshold, so that the second signal comprises information on a movement of the laser marker above the predetermined threshold; and
wherein the predetermined threshold is set above a frequency of intended motion of the surgical instrument.

14. The surgical tool system according to claim 13, wherein the first signal comprises information on the motion of the handheld surgical instrument within a range of frequencies including the frequency of intended motion of the surgical instrument.

15. The surgical tool system according to claim 14, wherein the processing circuit is configured to control the actuator to move the movable platform based on the first signal and the second signal so that the intended motion of the surgical instrument is uncompensated by the movement of the movable platform.

16. The surgical tool system according to claim 15,
wherein the processing circuit is configured to generate an output signal based on the first signal and the second signal, the output signal excluding frequencies at or below the predetermined threshold; and
wherein the processing circuit is configured to control the actuator to move the movable platform based on the output signal.

17. A method of operating a handheld surgical instrument, the method comprising:
using a laser source to emit a laser beam to generate a laser marker on a surface;
detecting, using an inertial measurement unit, a motion of the handheld surgical instrument;
generating, using the inertial measurement unit, a first signal comprising information on the motion of the handheld surgical instrument detected; and
controlling, using a processing circuit, an actuator to move a movable platform, the movable platform holding a controlled tool tip, based on the first signal generated by the inertial measurement unit and a second signal generated by a vision unit based on a movement of the laser marker, so that the movement of the movable platform holding the controlled tool tip at least partially compensates a tremulous motion of the handheld surgical instrument.

18. The method according to claim 17, the method further comprising using a beam splitter to separate the laser beam to form the laser marker and a further laser marker on the surface, wherein the second signal is generated by the vision unit based on the movement of the laser marker and a movement of the further laser marker.

19. The method according to claim 17, wherein the laser marker is of any shape selected from a group consisting of a circular shape, a rectangular shape, a T-shape, and a cross shape.

20. The method according to claim 17,
wherein the first signal comprises information on the motion of the handheld surgical instrument within a range of frequencies including a frequency of intended motion of the surgical instrument; and
wherein the second signal comprises information on the movement of the laser marker above a predetermined threshold, the predetermined threshold set above the frequency of intended motion of the surgical instrument.

* * * * *